United States Patent [19]

Maggard

[11] Patent Number: 5,362,965
[45] Date of Patent: Nov. 8, 1994

[54] INDIRECT METHOD FOR DETERMINING OXYGENATE CONTENT USING NEAR-INFRARED ABSORPTION SPECTRA

[75] Inventor: Steven M. Maggard, Lake Jackson, Tex.

[73] Assignee: Ashland Oil Inc., Ashland, Ky.

[21] Appl. No.: 59,700

[22] Filed: May 10, 1993

Related U.S. Application Data

[63] Continuation-in-part of Ser. No. 890,048, May 27, 1992, abandoned.

[51] Int. Cl.$^5$ ............................................. G01N 21/35
[52] U.S. Cl. .............................. 250/339.12; 250/343
[58] Field of Search ............ 250/339, 340, 343, 339.12

[56] References Cited

FOREIGN PATENT DOCUMENTS 2136118 3/1984 United Kingdom .

OTHER PUBLICATIONS

"Detection of Methanol in Gasolines Using Near-Infrared Spectroscopy & an Optical Fiber", Applied Spectroscopy, vol. 41, No. 8, 1987, pp. 1388–1392.

"Detection of Ethanol in Wines Using Optical-Fiber Measurements & Near-Infrared Analysis", Applied Spectroscopy, vol. 42, No. 6, 1988, pp. 1106–1111.

"Determination of Carbon–Hydrogen Groups in High Molecular Weight Hydrocarbons", A. Evans, R. R. Hibbard and A. S. Powell Analytical Chemistry, vol. 23, No. 11, Nov. 1951, pp. 1604–1610.

Primary Examiner—Constantine Hannaher
Attorney, Agent, or Firm—Richard C. Willson, Jr.

[57] ABSTRACT

Method for determining oxygenate content and/or octane of hydrocarbon fuels suitable for automotive vehicles. Selecting nanometer frequencies in the range 1,300 to 1,350 reduces the temperature dependence of calibration equations that predict values representative of both oxygenate content and octane. This can be further improved by using only derivatives of selected temperature-dependent frequencies in addition to those in the 1,300 to 1,350 nanometer range. The selected frequencies preferably primarily correspond to C-H vibrational modes.

22 Claims, 15 Drawing Sheets

INDIRECT METHOD FOR DETERMINING OXYGENATE CONTENT USING NEAR-INFRARED ABSORPTION SPECTRA

This application is a continuation-in-part of U.S. Ser. No. 890,048, filed May 27, 1992, now abandoned.

CROSS REFERENCE TO RELATED APPLICATIONS

U.S. patent application Ser. No. 506391, filed Apr. 9, 1990 (Attorney Docket No. 6362AUS); U.S. Pat. No. 4,963,745, issued Oct. 16, 1990, relates to the general field of the present invention, as does U.S. patent application Ser. No. 698,411, filed May 10, 1991 (Attorney Docket 6379AUS); and U.S. Pat. No. 5,145,785, issued Sep. 8, 1992, (Attorney Docket No. 6384AUS) relates also to this general field of the present invention.

BACKGROUND OF THE INVENTION

1. Field of the Invention:

This invention relates to the determination of physical or chemical properties of compositions by means of near-infrared absorption bands. More specifically, this invention relates to compositions that involve hydrocarbons and substituted hydrocarbons, along with oxygenates such as ethers and alcohols. Still more specifically, this invention relates to octane determinations of oxygenate-containing fuels and percents by volume or by weight of oxygenate content of such fuels.

Oxygenate content for purpose of this specification and claims includes the oxygen that would be contained in hydrocarbons. Examples of typical oxygen-containing hydrocarbons that are particularly useful for automotive fuels are: alcohols, such as ethanol, methanol, butanol, iso-butanol, t-butanol, and iso-amyl alcohol; and ethers, such as methyl t-butyl ether, ethyl t-butyl ether, methyl iso-amyl ether, and ethyl iso-amyl ether.

2. Description of the Prior Art

The prior art as shown in the following U.S. patents shows that it is possible to find near-infrared absorption bands which correlate with octane. Note in this regard, European Patent Application (Publication number 0285251) 88301646.1 of Lambert et al. of BP Oil International Limited, filed Feb. 25, 1988. Heat content of certain fuel compositions and number of methyl groups per molecule were also shown to be correlatable to certain near-infrared absorption bands.

"Use of Indirect Multi-Variable Calibration Equations for Quality Control of Agricultural Products by Near-Infrared Spectroscopy," G. Puchwein and A. Eibelhuber (Mikrochim. Acta) Wein), (1986; It 43–51) teach a computer program for calibrating an instrument. The program picks relevant frequencies for spectral data for part of a set of samples with which to calibrate an instrument and then validates with respect to the remaining samples not used to establish to calibration.

A near-infrared regression model for octane measurements in gasoline which contain MTBE was published in a book of proceedings by the American Chemical Society, Division of Fuel Chemistry, in Volume 35, Number 1, Pages 266–275 which was written by Steven M. Maggard and also presented by him at the 199th American Chemical Society National Meeting in Boston, Mass. on Apr. 22–27, 1990. Specifically disclosed in this paper and presentation is the use of methyne t-butyl combination bands, including overtones, in models to predict octanes of MTBE-containing gasoline compositions.

B. G. Osborne, in an article entitled, *Calibration of Instrument for Near-Infrared Spectroscopy*, 48 Spectroscopy, Vol. No. 4, pages 48–55), discloses in detail the steps for establishing simple correlations by multiple linear regression and also the use of derivatives of linear terms. Validation of calibration curves are discussed: specifically how particular wavelengths are chosen to establish the terms in multiple linear regression equations, along with the statistical significance of a particular calibration sample. This method can be used in this invention for the purpose of defining the calibration equations with which one can calculate oxygenate content or octane from absorption spectral data.

Still other methods for determining calibration equations are those discussed in Analytical Chemistry Journal, volume 60, pages 1193–1202 (1988) by David M. Haaland and Edward V. Thomas. The principles of inverse least squares, partial least squares, classical least squares, and principle component regression analysis are disclosed. All of these methods are useful in the instant invention.

Jeffrey J. Kelly and James B. Callis in Analytical Chem. 1990, volume 62, pages 1444–1451, in an article entitled, *Nondestructive Analytical Procedure for Simultaneous Estimation of Major Classes of Hydrocarbon Constituents of Finished Gasolines*, discloses how frequencies are selected and how the statistical significance of a particular set of frequencies are determined. Specifically stepwise multilinear regression was performed. Mathematical treatments of the data prior to multiple regression analysis, such as base-line drift correction, end-point smoothing, and first and second derivatives, were explored to determine best-fit linear-regression equation for each data set. The inter-correlations between the regression wavelengths were calculated, and the wavelengths that exhibited high correlations were eliminated in order to reduce information redundancy and over fitting. This selection of wavelengths did not take into account the degree of temperature dependence.

Jeffrey J. Kelly, C. H. Barlow, T. M. Jinguji, and J. B. Callis in an article entitled, *Prediction Of Gasoline Octane Numbers from Near-Infrared Spectral Features in the Range 660–1215 nm*, published in Analytical Chemistry, Volume 61, No. 4, Feb. 15, 1989, on page 313–319, disclose use of multi-variable analysis of spectra to predict ASTM motor-determined octane numbers. Independent multi-variable analysis using partial leased-squares (PLS) regression analysis is also disclosed. The key step in the setting up of the calibration equations appears to be that high correlations were eliminated in order to reduce information redundancy and over-fitting.

U.S. Pat. No. 4,800,279 to Hieftje et al. (Jan. 24, 1989) teaches use of near-infrared (NIR) to predict physical properties of certain hydrocarbon mixtures.

Currently, programs exist to find and optimize correlations between near infrared absorption spectra for a particular material, or their mathematical transforms, and physical and chemical properties of such a material. Specific properties that are known to be indirectly determinable from near infrared spectra include: octane; cetane; enthalpy or heat content; percent water in grain; a PIANO analysis; and the like. Currently, the method followed in the art as presently practiced and known, is to essentially look for spectral properties that correlate with some property of interest, such as a physical or chemical property. This is both reasonable and logical. This approach is described in "The Analyst", Volume 107, published October 1982, pages 1282–1285 in an article entitled, *Determination of Ethanol in Gasoline Mixtures by Near Infrared Method*, by Jane L. Wong and Bruno Jaselskis. The article found that 1580 nanometers was a particularly useful absorption frequency for determining the % ethanol content of gasohol. However, neither suggested nor disclosed is the fact that a finite difference derivative such as discussed in Example 1 when taken at the first and higher levels of derivative can result in a two fold decrease in error from temperature dependence when the value of the dependent variable calculated. Preferably, in the case of a second derivative of absorbance in the range of 1576 to 1596 for a calibration equation that predicts volume percent oxygenate content the segment preferably in integral multiples of 2 nanometer lengths is in the range of 4 to 30, and more preferably 15 to 25 and the gap is an integer in the range, of 0 to 5 and more, preferably 0.

Alternatively, one would expect that the most intense bands representative of the functional groups of interest; e.g., in the case of oxygen-containing gasoline components, a CO or OH characteristic vibrational frequency in the near infrared would be of most interest. Examples of such bands for OH are in the first overtone near 1410 nanometers, in the second overtone near 1000 nanometers, and for combinations bands near 2000 nanometers. These frequencies are most likely to give the highest correlation to percent by volume oxygenate content. These frequencies are mentioned by L. G. Weyer in "APPLIED SPECTROSCOPY REVIEWS", Volume 21 (Issues 1 and 2), pages 1–43, published 1985 in an article entitled, *Near-Infrared of Organic Substances*.

This invention discloses the surprising discovery that there are particularly useful bands for determining oxygenate content of gasoline blends, that includes ethers and/or alcohols, that are overlooked in the "Applied Spectroscopy Reviews". One must use the absorption frequency in the range of 1,300–1,350, and preferably 1,310 through 1,340 nanometers. Once one limits the contribution in the correlation equation to expressly include those in this frequency range, one finds that the correlation can lead to a substantially reduced temperature dependence.

This invention further discloses the discovery that there is a markedly decreased temperature dependence in the calculated dependent variable that corresponds to any chemical or physical property. For example, there is a reduced temperature dependency in calculated octane or cetane when one correlates a derivative of absorption at unexpected frequencies in the range 1568 to 1596 preferably 1576 to 1592 nanometers. This becomes particularly important in those cases in which the spectral properties for the components making up the mixture are markedly temperature dependent. Such compounds are often those that give rise to hydrogen bonding such as methanol, ethanol, and other alcohols. The temperature dependence of any near infrared absorption results from a complex array of interactions including dipole-dipole interactions; including hydrogen bonding; density effects; and refractive index changes. Though 1580 has been reported as useful by Wong and Jaselskis, there was no suggestion or disclosure that as much as a ten fold decrease in temperature dependence could be achieved by taking finite difference derivatives, such as for example, shown in Examples III and IV.

That different functional groups have different degrees of temperature dependence makes multi-component analysis by NIR especially complex and difficult. Dipolar moments interacting with other dipolar moments tend to be temperature dependent. The variation in dipolar moments of various functional groups give rise to different degrees of temperature dependence.

Prior art analysis of composition by means of NIR, such as a PIANO which stands for the group acronym for: paraffins, isoparaffins, aromatics, naphthenes, and olefins involve determinations based upon total amount of those molecules taken together that are respectively members of some one of these groups. They did not determine the specific volume percent of a particular specie within any one of the various groups. Previous determinations of PIANO by NIR were limited to determining the compositions based upon groups of molecules rather than individual species. U.S. patent application Ser. No. 506,391, filed Apr. 9, 1990, to Maggard (Attorney Docket No. 6362AUS) discloses PIANO-NIR and the usefulness of PIANO bands for predicting octanes. Of course, use of techniques such as gas phase or liquid phase chromatography were able to isolate specific components of each of these species. The reason, however, that in an NIR-based determination, one is forced to deal with molecules by groups results from the extensive overlap with spectra from various species within a particular mixture. For example the CH bands of isoparaffins, and normal paraffins have large regions of absorption overlap. Consequently, to distinguish the contributions from one specie of a mixture separate from that contribution of another is very difficult, if not impossible. Attempts to do this become extremely complicated mathematically because one would have to determine each component's contribution to a particular band, and one would have to have enough bands so as to be able to distinguish how much of each specie was contributing to the various bands. If one had as many as ten unknowns, one would need at least nine different bands if all of the components had absorption bands that overlapped one another. J. D. Winefordner has done work detailing such requirements for such mixtures.

SUMMARY OF THE INVENTION

1. General Statement of the Invention:

This invention makes it possible to improve the reliability of NIR absorption spectra, both in its prediction of octanes or cetane values for automotive fuels where NIR absorption spectra for certain components that are highly temperature dependent are used in a linear calibration equation such as disclosed in either volume 60 of Analytical Chemistry Journal, Pages 1193–1202 (1988) or Volume 62 of Analytical Chemistry, Pages 1440–1451 (1990) Examples of such components are alcohols, but also determinations of oxgenate content due to the presence of alcohols or ether which have significant amounts of temperature dependence are also improved. In Example II, the economic consequences of accurately determining oxygen content is demonstrated.

Today it is possible to use a variety of wavelengths throughout a region to determine how well selections of wavelengths within a certain region can be put into a correlation equation to predict a physical or chemical property or composition. An example of such a graph is shown in FIGS. 7–9. It is important to understand that when one looks at such a plot, it is not an automatic and simple thing to pick out the frequencies to use in order to obtain optimal best correlations, because the correlations are dependent on what wavelengths have been included (or will be included) in the model and there are an extremely large number of potential wavelength combinations.

An absorption spectra of gasoline with and without oxygenates discloses readily where differences in absorption are greatest. However, these differences in absorbance are in the region of greatest temperature dependence. We have discovered that if one takes the derivative of the absorbance, one can use absorption bands in a region which appears to be both relatively flat and having a very small difference in absorptivity of the gasoline with and without the oxygenate which surprisingly in conjunction with other absorption bands can result in a correlation equation that has significantly lowered temperature dependence. For details see Example V. That oxygen content of ethers can be correlated to absorption bands in the 1308–1350 nanometer range was totally unexpected and previously unknown. This is still more surprising because the apparent contribution to the absorption spectra in the region of 1308–1346 nm is found to be small for both the OH and any ether bands that may otherwise be occurring. For example, it was found, that the increased absorption in the 1308 to 1346 nanometer range for oxygenated and regular unleaded gasoline due to the presence of oxygenates was small.

We have discovered that derivatives, including first and higher orders of certain absorption bands unexpectedly are not nearly so temperature dependent as derivatives of other bands or absorption bands of all frequencies that are not mathematically transformed, in terms of differences observed over temperature ranges for values of calculated dependent variables. This means that much of the band shifting that occurs as a result of temperature variations on the sample can be avoided. In the cases where bands overlap, any shifting relatively to one another can very adversely impact: the accuracy with which one can determine a composition. This is clear because it is necessary from the absorption spectra to determine how much each species is contributing to various bands. Their contributions in the presence of temperature dependence will vary in very complex and difficult ways to anticipate accurately.

Not only was this unexpected property of temperature independence or invariance of a derivative, especially and preferrably second order derivatives, of certain absorptions, found, but also that some of these same bands were very useful in determining weight and volume percents of oxygenates. The region of 1,300 to 1,350 nanometers has been found to be surprisingly advantageous to determining not only octane, but also percent by volume or weight of oxygenate-species, such as alcohols and ethers. this specification discloses also the discovery that calibrations made with derivatives of absorption can be correlated to predict properties like octane and oxygenate content.

In summary, disclosed is the discovery of how to select bands appropriate for determining oxygenate content, that depends upon the fact that derivatives of certain frequency bands tend generally to be significantly more temperature independent than derivatives at other bands, and certain of those bands whose derivatives are found to be temperature independent also can correlate well with composition.

With increasing usages of alcohols and ethers in gasoline blends, the temperature dependence of hydrogen bonding and band shifting in the near-infrared has prior to this time made it difficult to determine reliable correlations between octane and alcohol-containing blends. This is true especially in those situations where determinations are made using NIR absorptions and temperature is not a readily-controlled variable.

It is a surprising aspect of the present invention that errors due to the temperature dependence of certain hydrocarbon and substituted hydrocarbon frequencies are substantially minimized by the use of derivatives, such as first and higher orders; such as 1st through 10th, preferrably 1st and 2nd.

The following paragraph from column 2, line 64 through column 3, line 6 of U.S. Pat. No. 4,963,745 to Steven M. Maggard (to the Assignee of the present invention, attorney docket 6353AUS), which is incorporated by reference into the present application:

2. Utility of the Invention:

The invention will be useful in the blending of gasoline, less preferably diesel fuels (octane number) and jet fuels, e.g. JP4, both in refineries and in large fuel storage terminations. Blending can be into storage tanks, tank trucks, rail cars, barges, or other transportation vehicles. An allowance for octane depletion during transportation based on expected weather conditions can also be included in determining the target oxygenate for blending. Additionally, the invention will be useful for monitoring gasoline quality at retail outlets to assure quality control specifications.

The following is from U.S. Ser. No. 506,391 filed Apr. 9, 1990 (attorney docket 6362AUS), page 7, lines 14+.

The techniques of the present invention are also highly useful for the objectives of aforementioned co-pending U.S. Ser. No. 402,959 filed Sep. 1, 1989 relating to the determination of research, motor and pump octane (also including cetane number of diesel fuels).

The flow may flow substantially intermittently or continuously past the point where the measurements are being made. The mathematical function may be a first, second, or third, etc. derivative of said absorption of said band being measured, the fuel may preferably be a gasoline blending stream, and the octane measured may preferably be research octane, more preferably motor octane, and most preferably pump octane.

The signal may control a fuel blending system feeding blending components having different oxygenate content into a common zone, whereby a fuel product having a desired octane is produced. (Where octane has been expressed in U.S. Ser. No. 402,959, the teachings are equally applicable to oxygenate content.)

DESCRIPTION OF THE PREFERRED EMBODIMENTS

BRIEF DESCRIPTION OF THE DRAWINGS

FIG. 1 shows the weightings which resulted from the 5 latent variable PLS model on the second derivative of absorbance data. FIG. 2 is an expansion of the weightings shown in FIG. 1 near 1580 nm. Note that the weightings near 1580 nm are nearly zero which indicates that they are not very important to this model. (The abscissa is wavelength in all of the Figures.)

FIG. 3 shows a plot of the autoscaled 6 latent variable PLS model weightings obtained on second derivative of absorbance data. Note that the weightings near 1580 nm do not appear to contribute more information than most of the other wavelengths in the model.

FIG. 4 shows the weightings developed during the PLS model on the baseline offset corrected absorbance data without autoscaling. The weightings near 1580 nm again do not appear as significant as other wavelengths in the model.

FIG. 5 is an expansion of the weightings shown in FIG. 1 near 1580 nm.

FIG. 6 shows the weightings of the 6 factor PLS model on baseline corrected absorbance data using autoscaling. Note relatively low weightings in the area near 1580 nm.

FIG. 7 shows a plot of the correlation spectrum versus wavelength (the correlation at each wavelength) for the first wavelength selection of the forward stepwise regression model expanded in the region near 1580 nm. Note that this area has a near zero correlation with (R+M)/2 octane.

FIG. 8 shows the correlation spectrum versus wavelength for the first wavelength selection of the second derivative of absorbance model near 1580 nm. Note that this area shows a moderate correlation of about 0.8 in this region, but there are others with correlations that are higher, for example those near 1525.

FIG. 9 shows the correlation spectrum versus wavelength for the second wavelength selection of the second derivative of absorbance model after the methyne band at 1224 nm has been included in the model. Note suddenly, there is an extremely high correlation with (R+M)/2 octane observed near 1580 nm.

Examination of the weightings used in the PLS models again showed very low weightings in the region of 1316 nm for the data without autoscaling and only modest weightings in the vicinity of 1316 for the autoscaled weightings. This is shown graphically in FIGS. 10, 11, 12, and 13.

Figure 1:
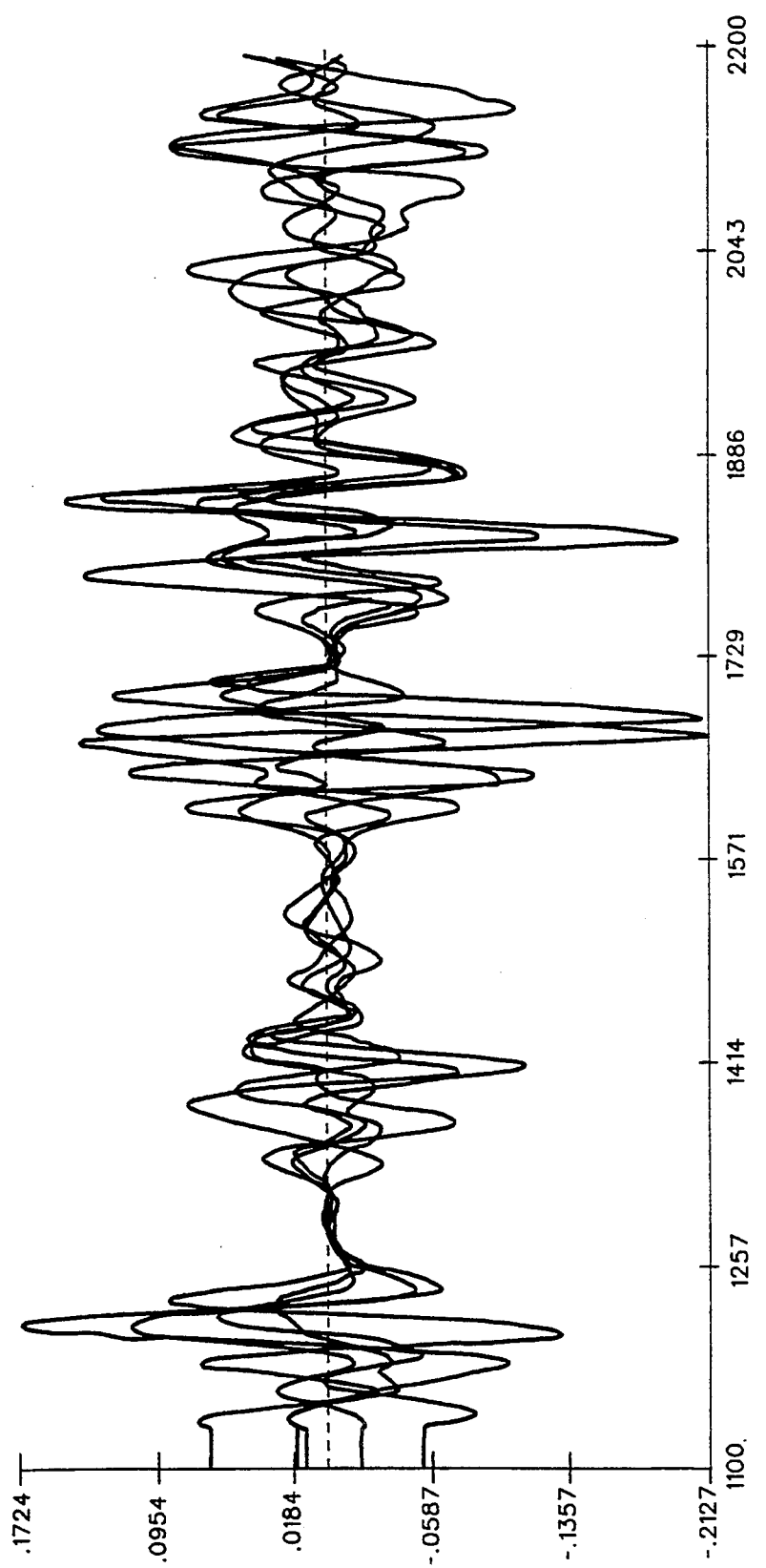
FIG. 1–15 are discussed in the Examples.
Figure 2:
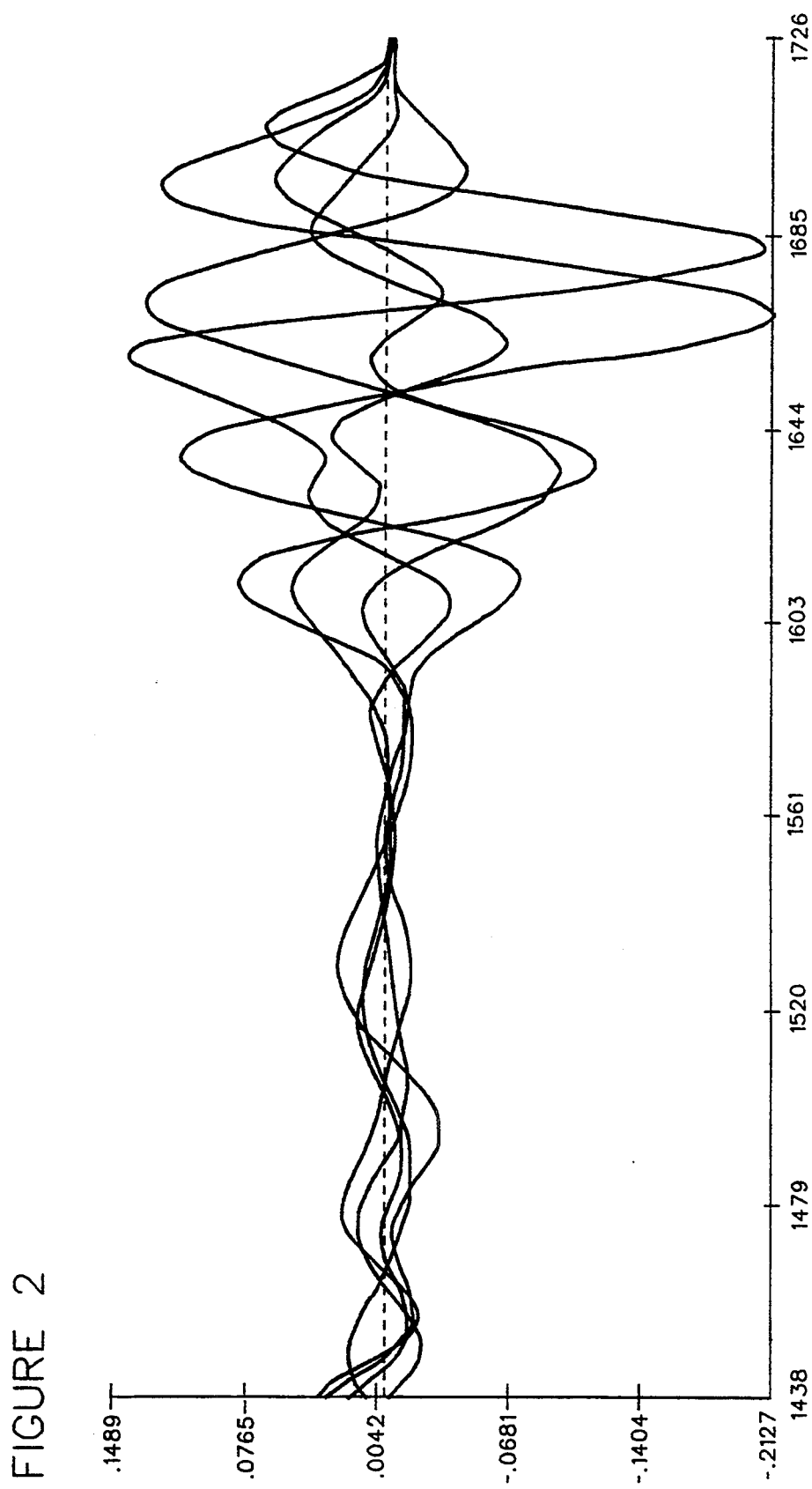
Figure 3:
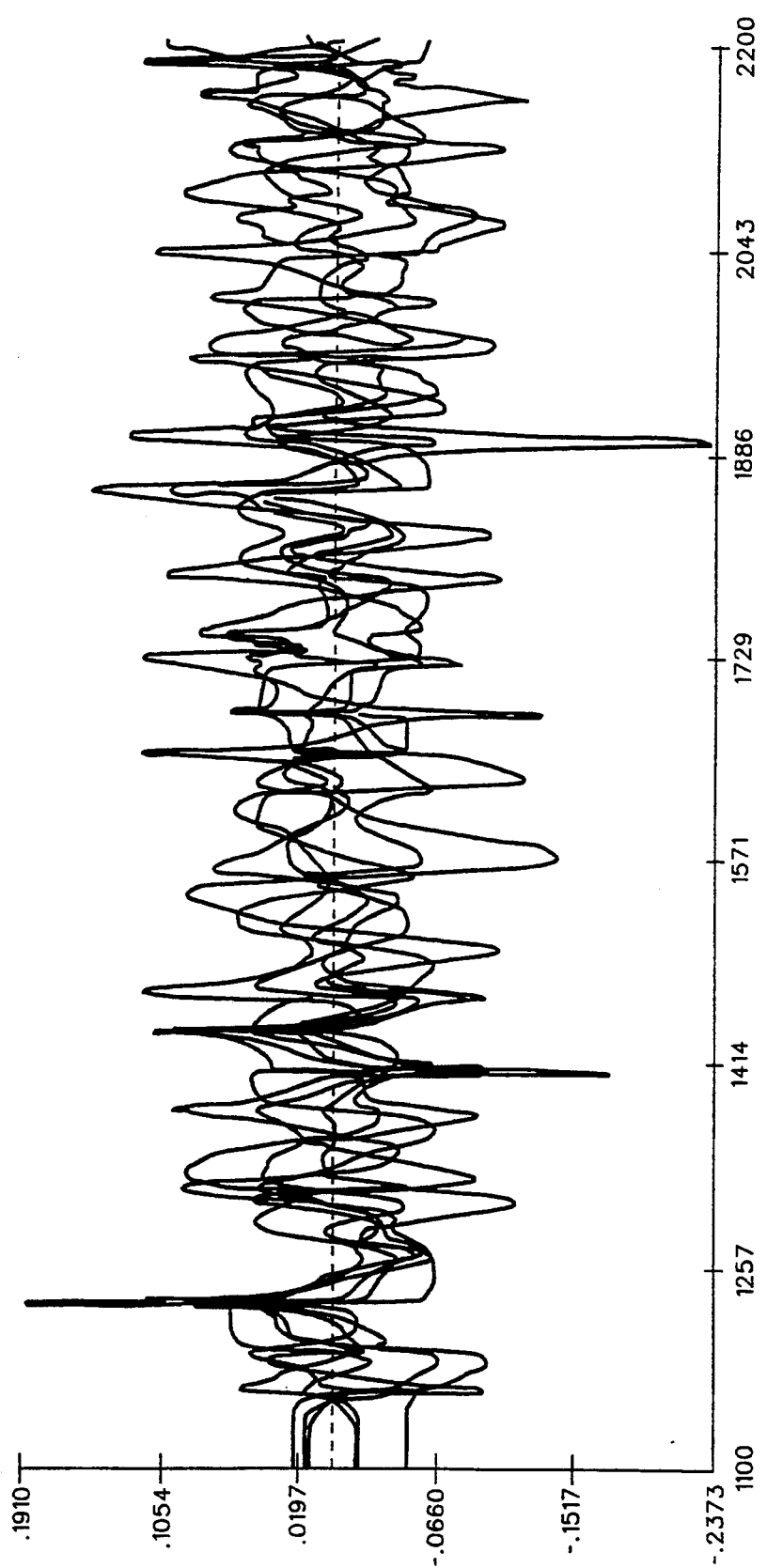
Figure 4:
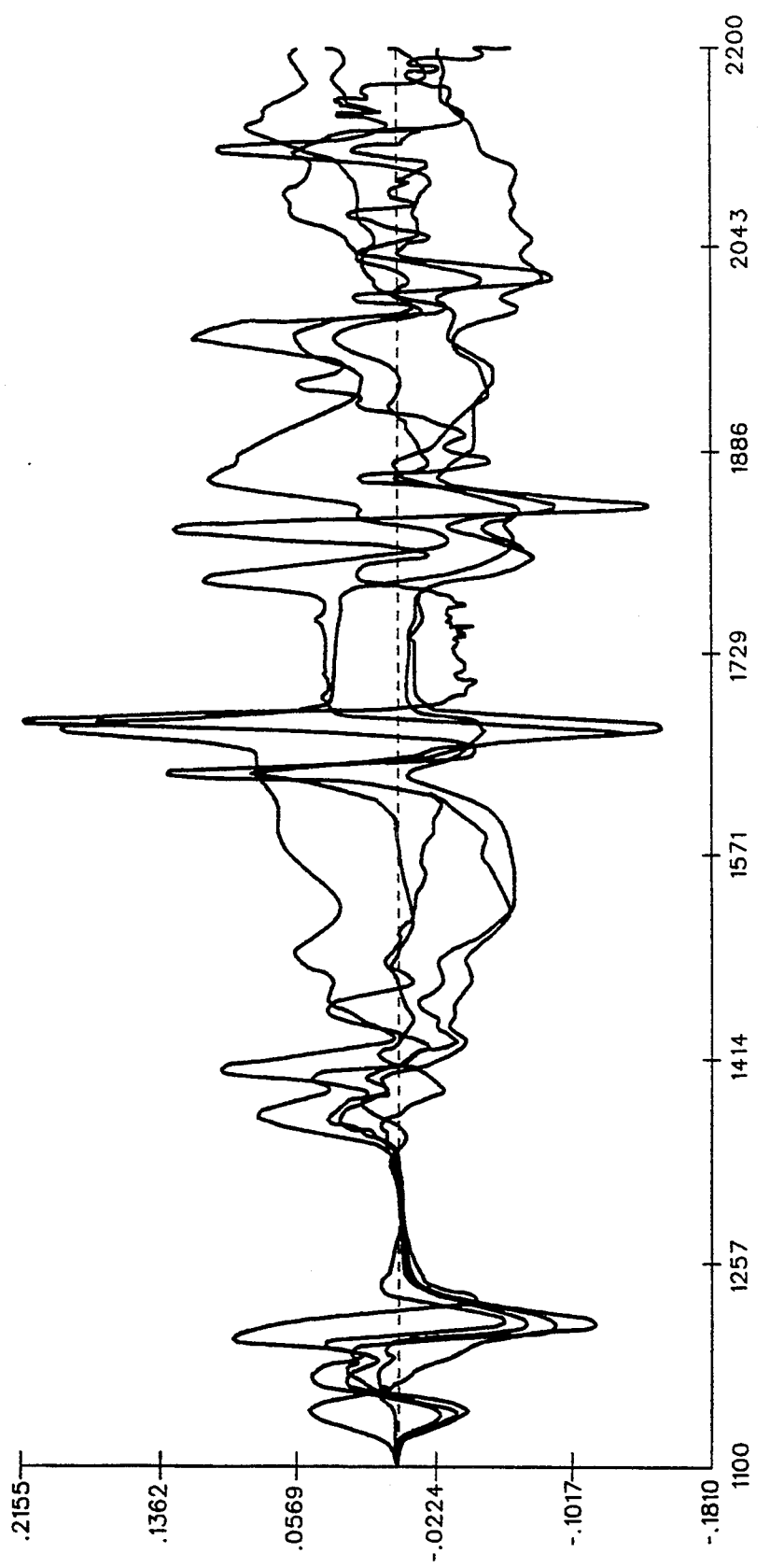
Figure 5:
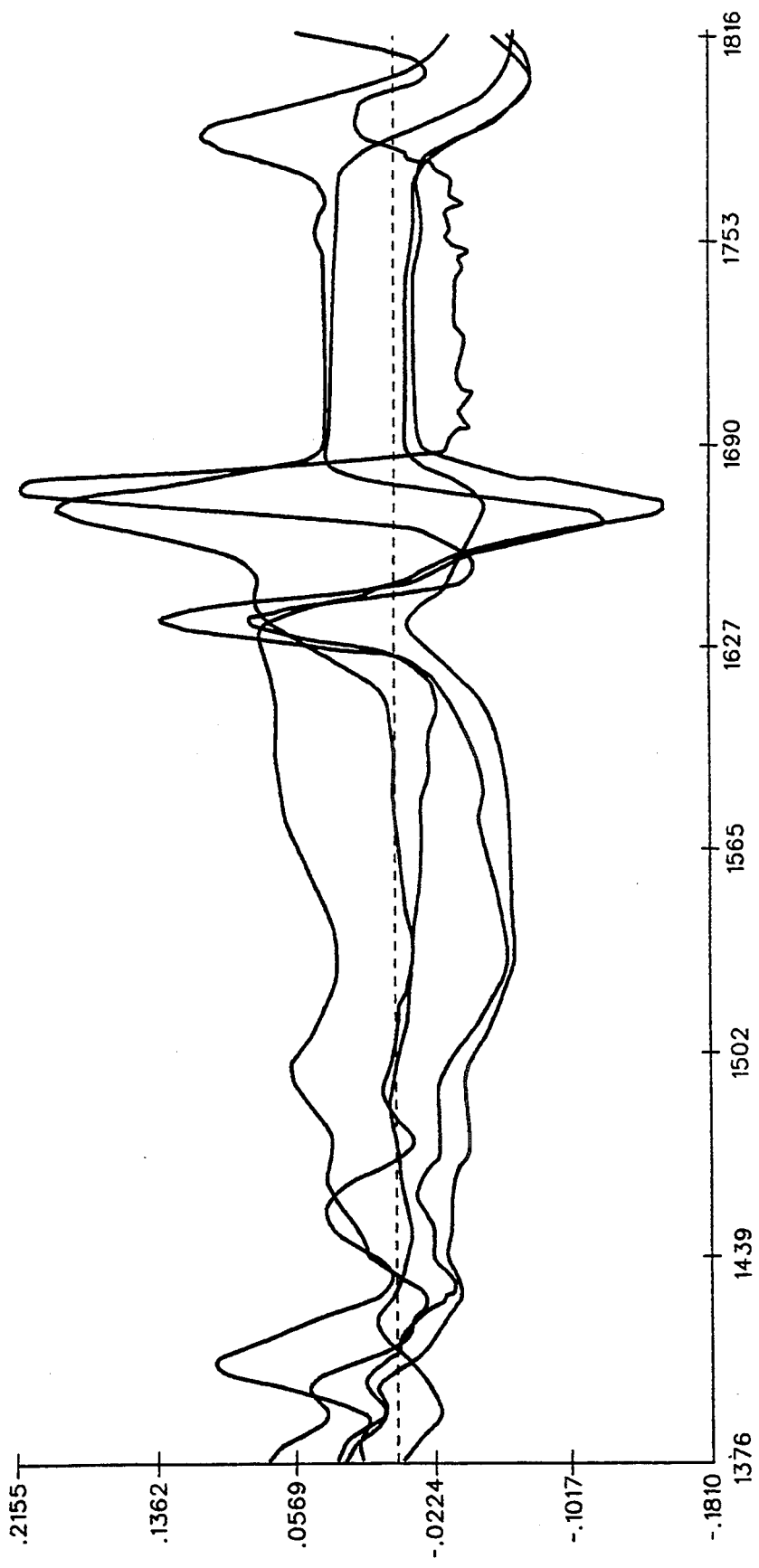
Figure 6:
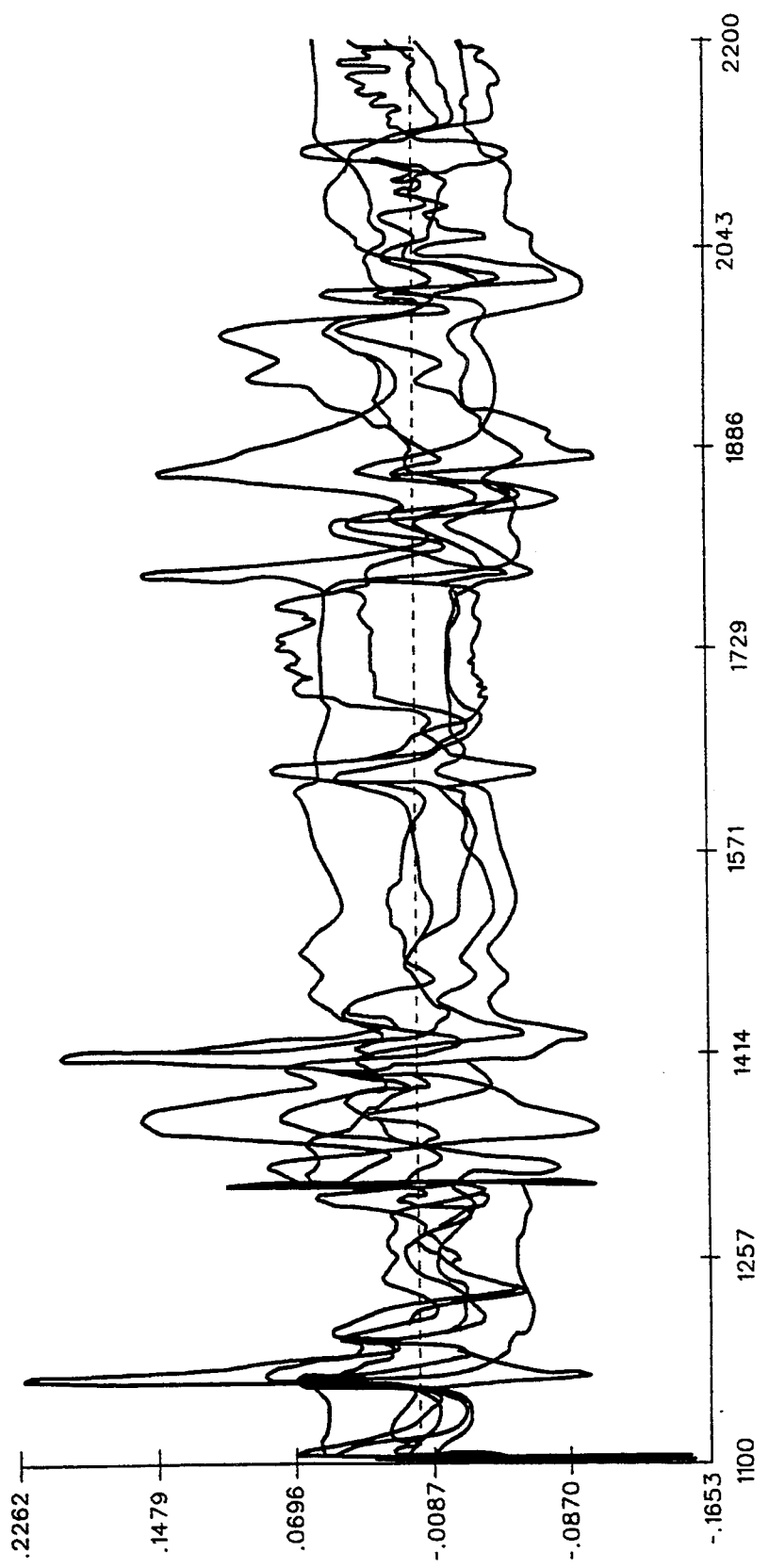
Figure 7:
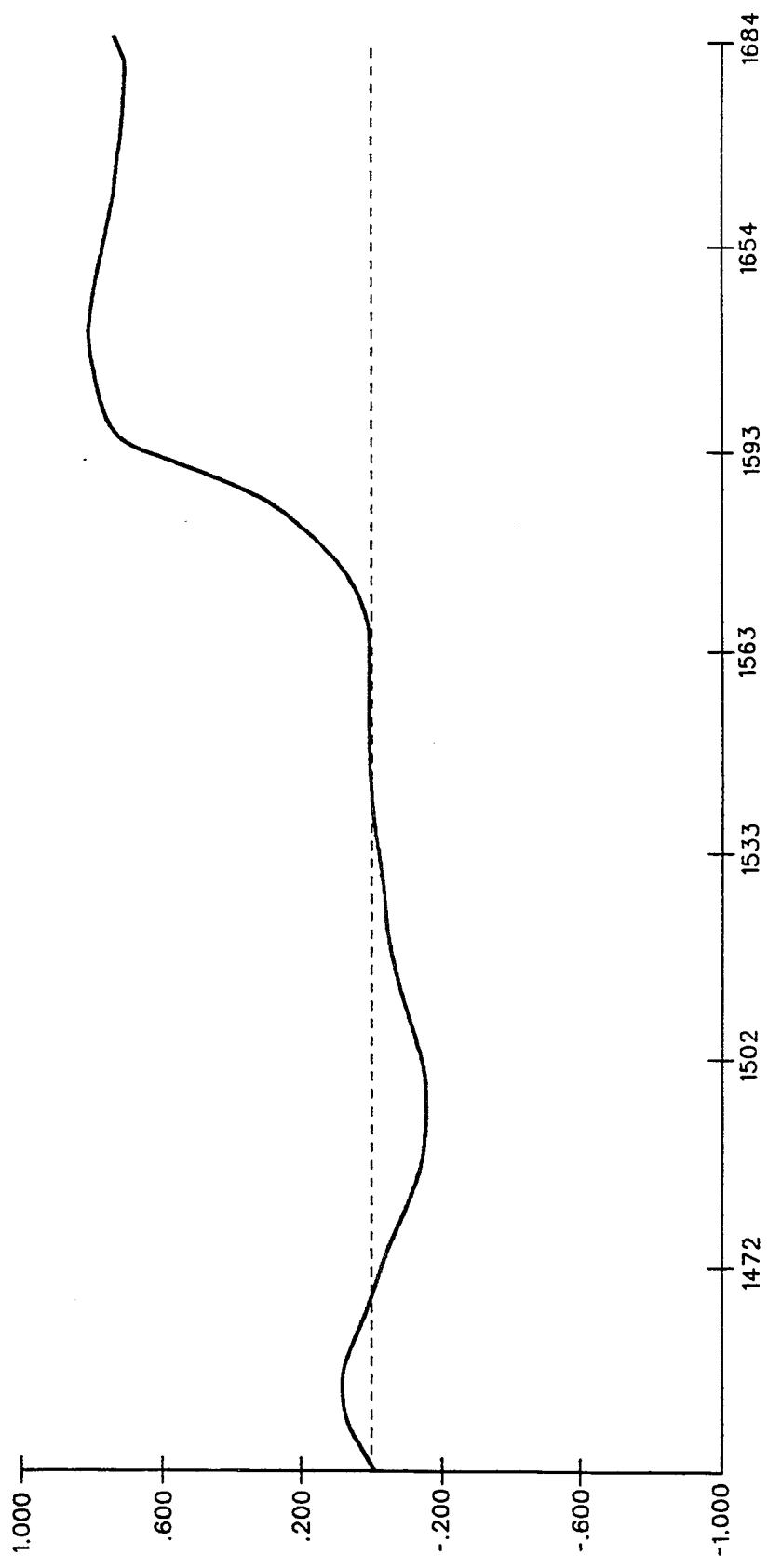
Figure 8:
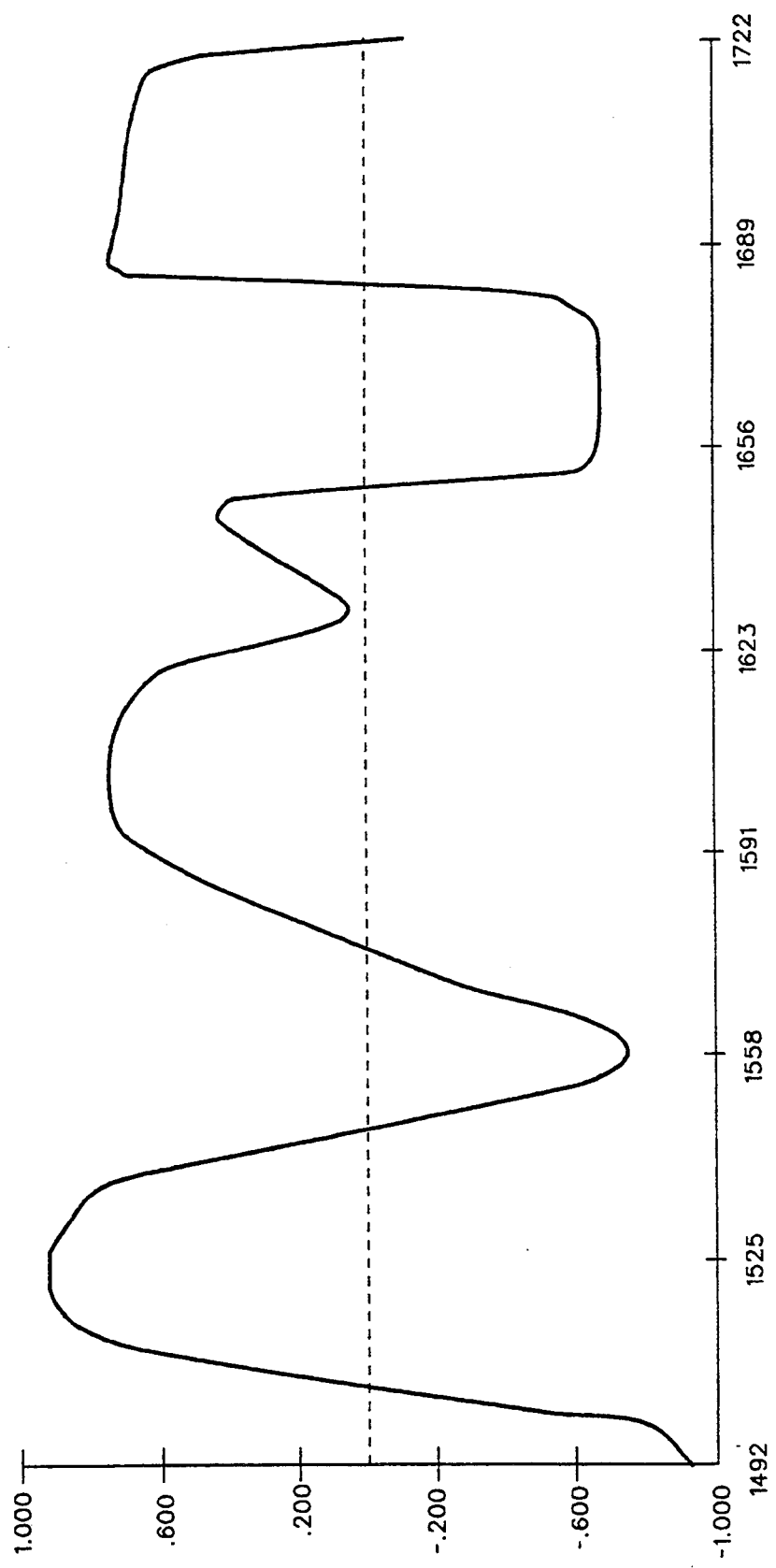
Figure 9:
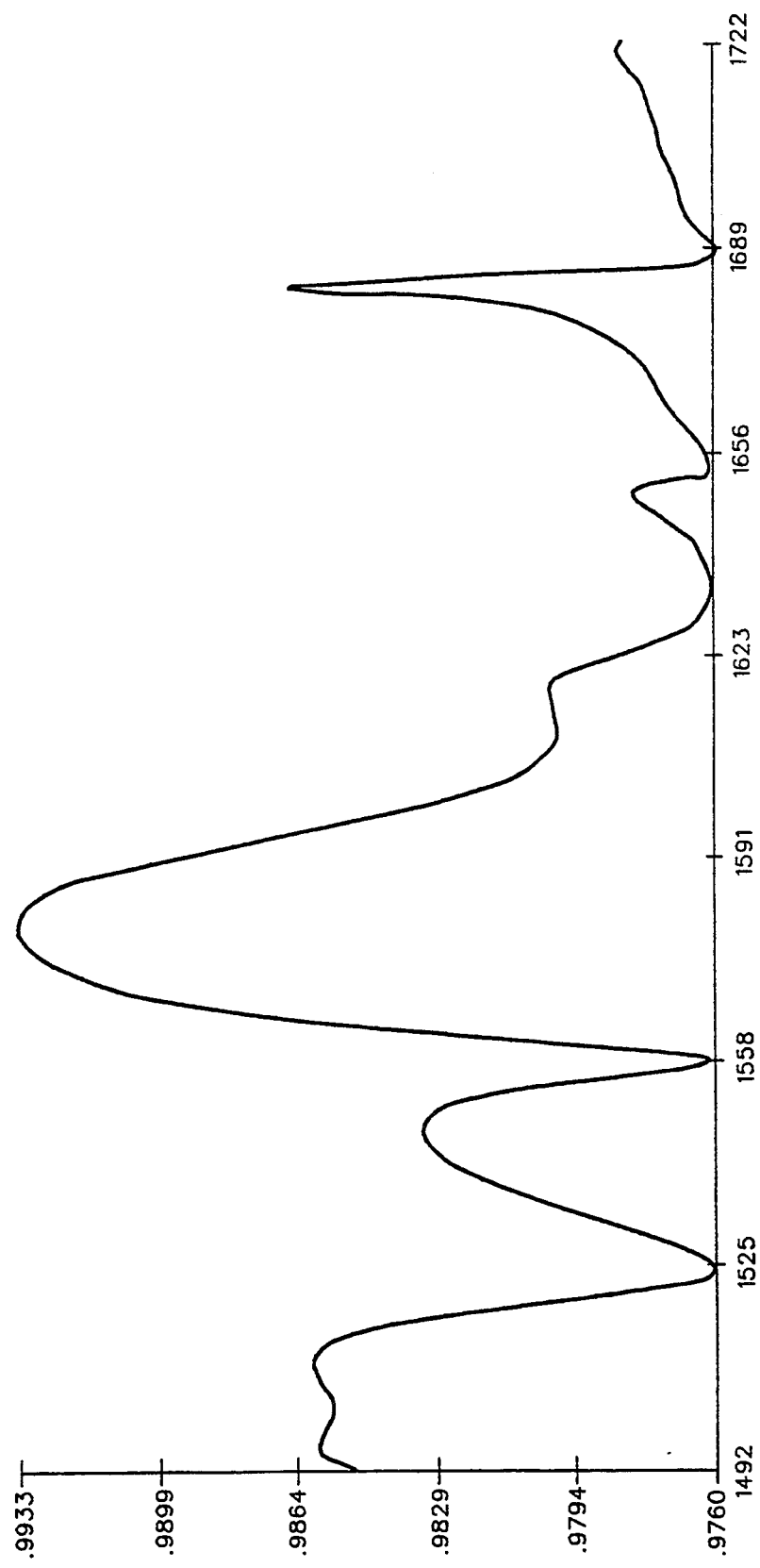
Figure 10:
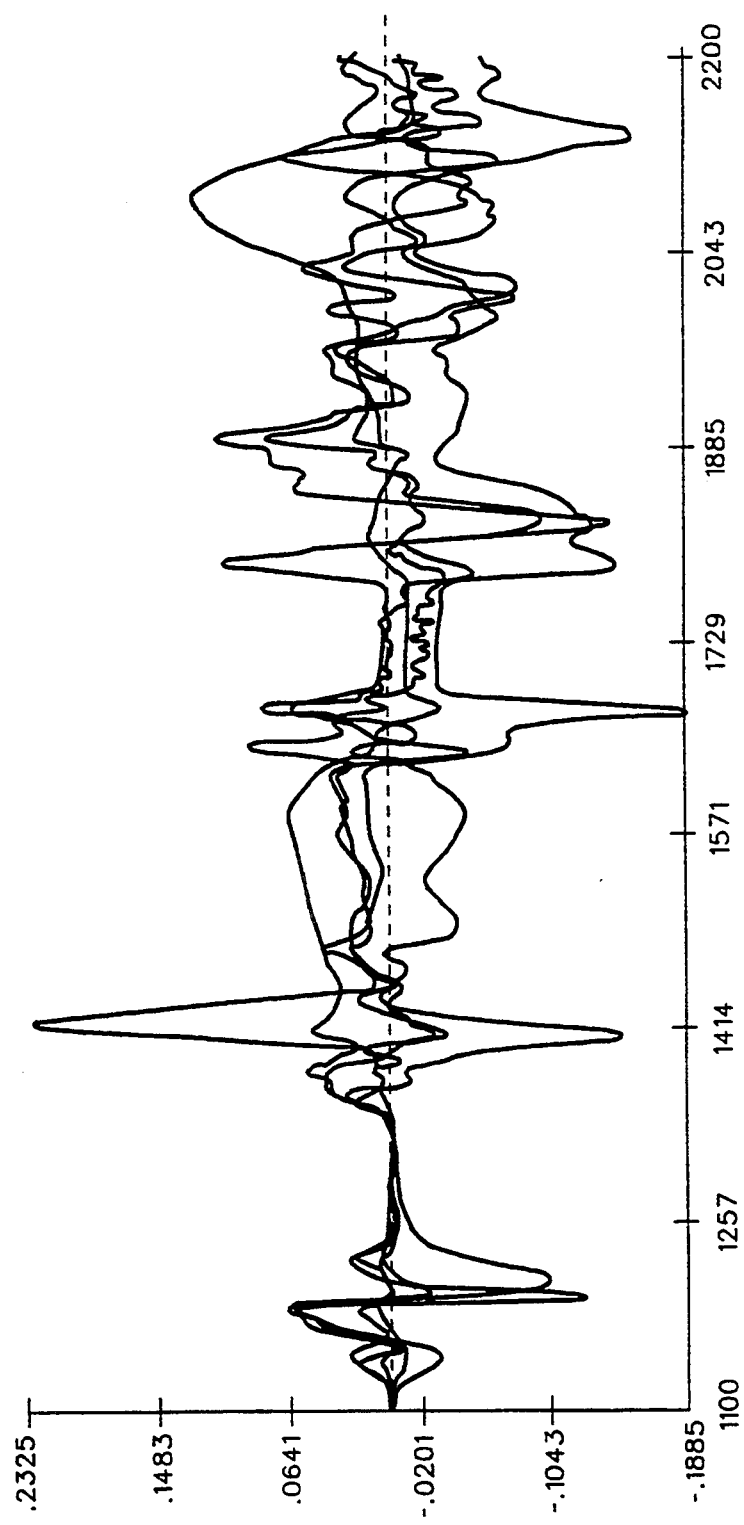
Figure 11:
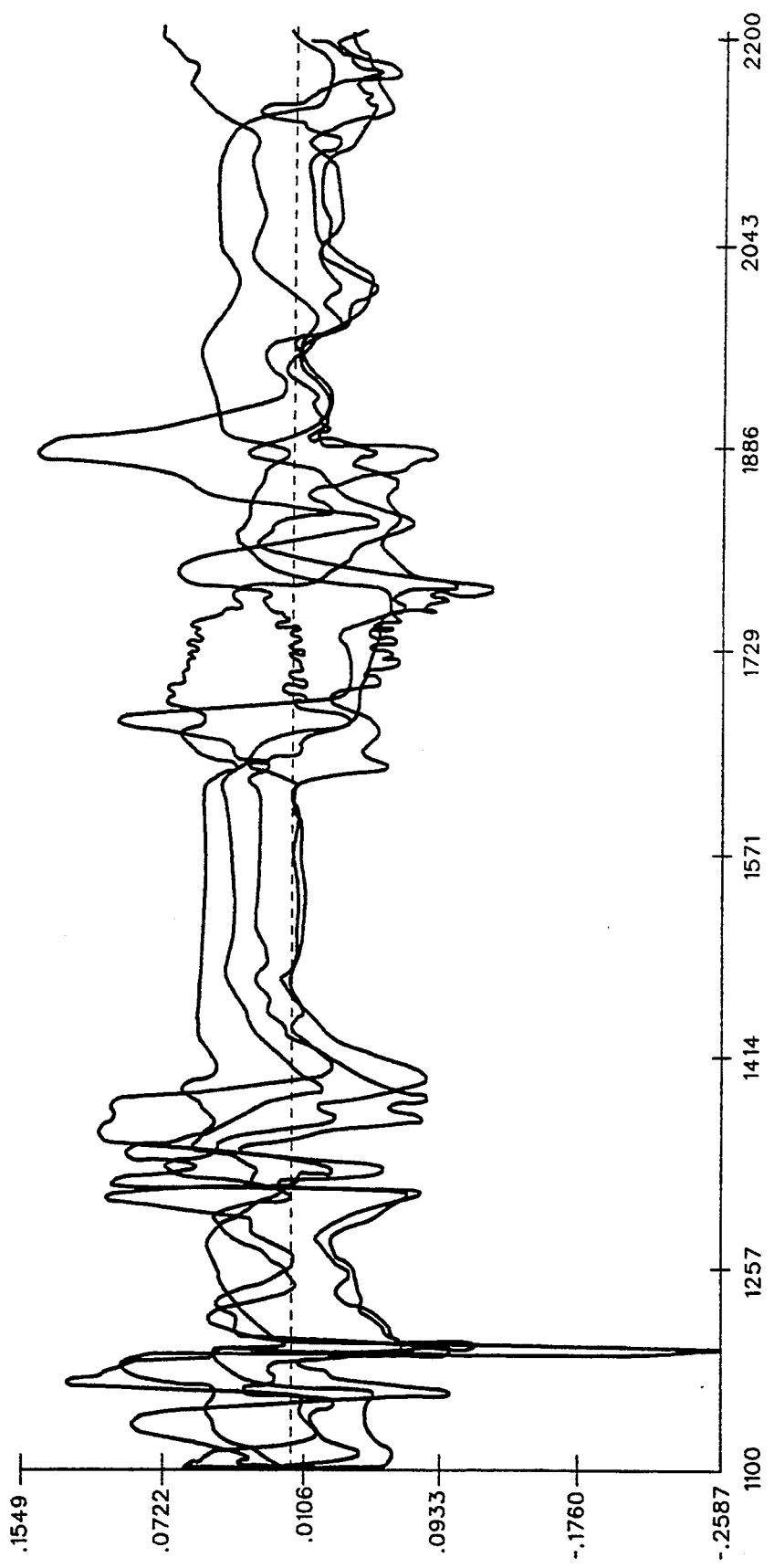
Figure 12:
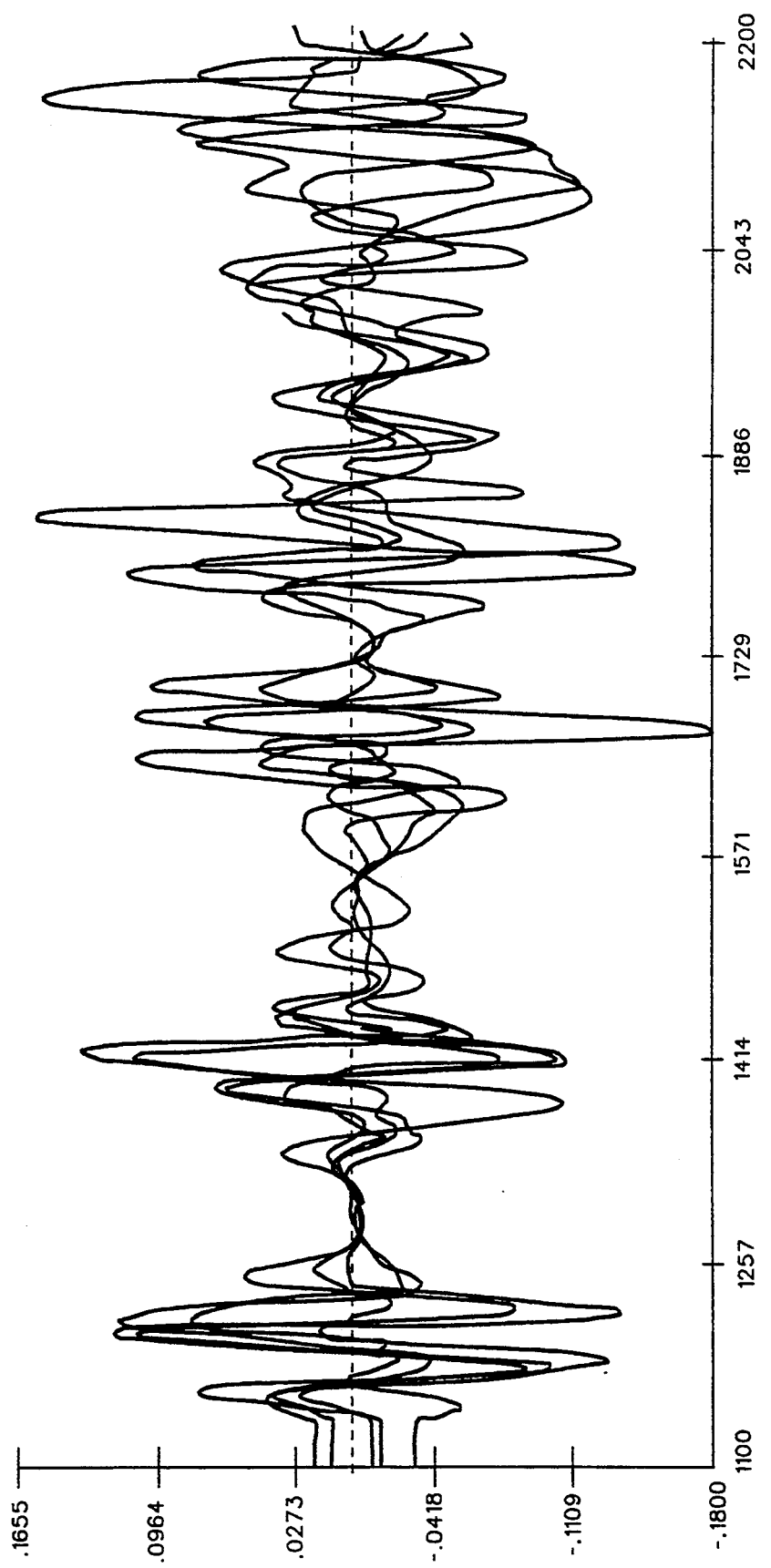
Figure 13:
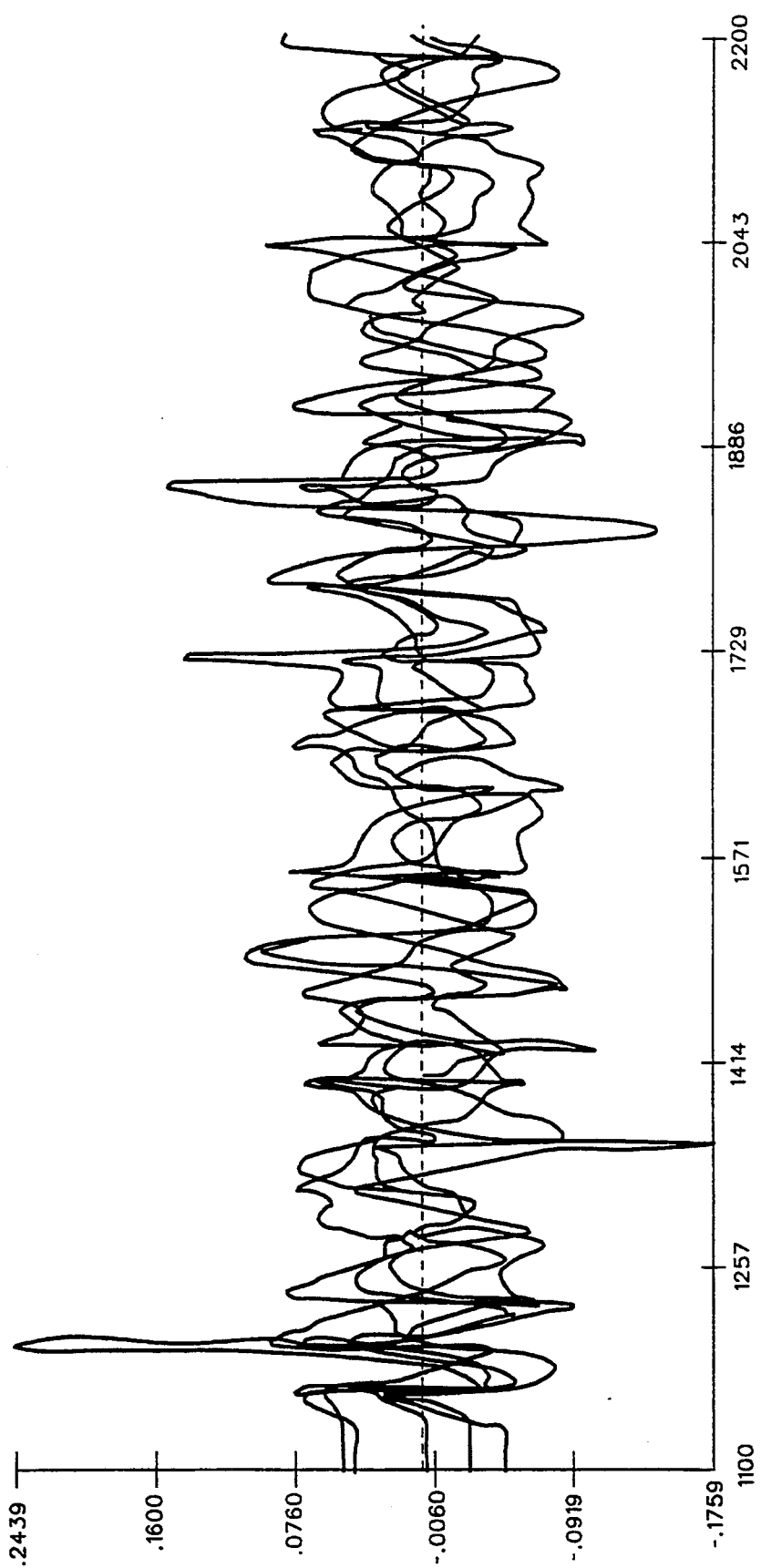
Figure 14:
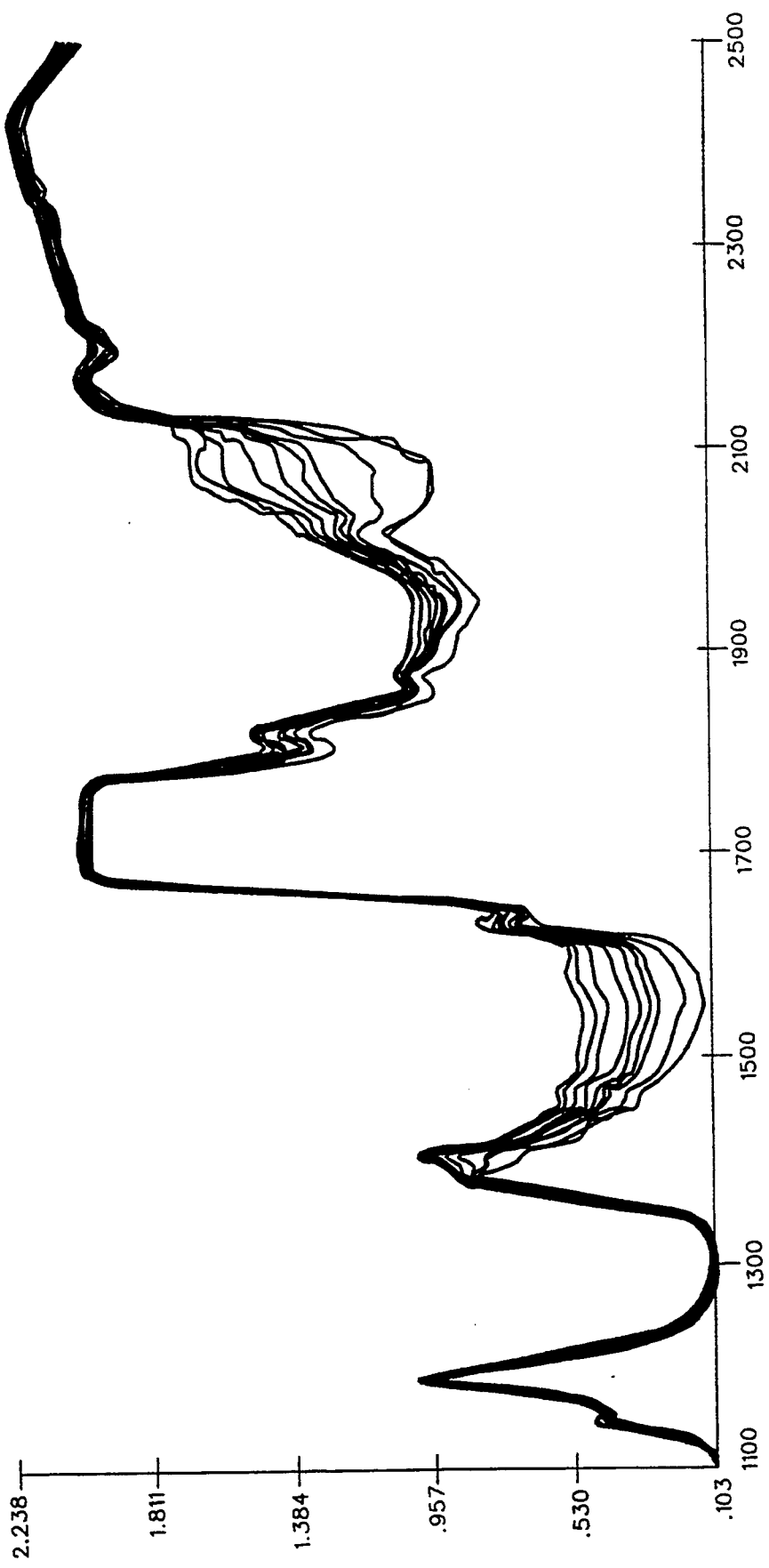
Figure 15:
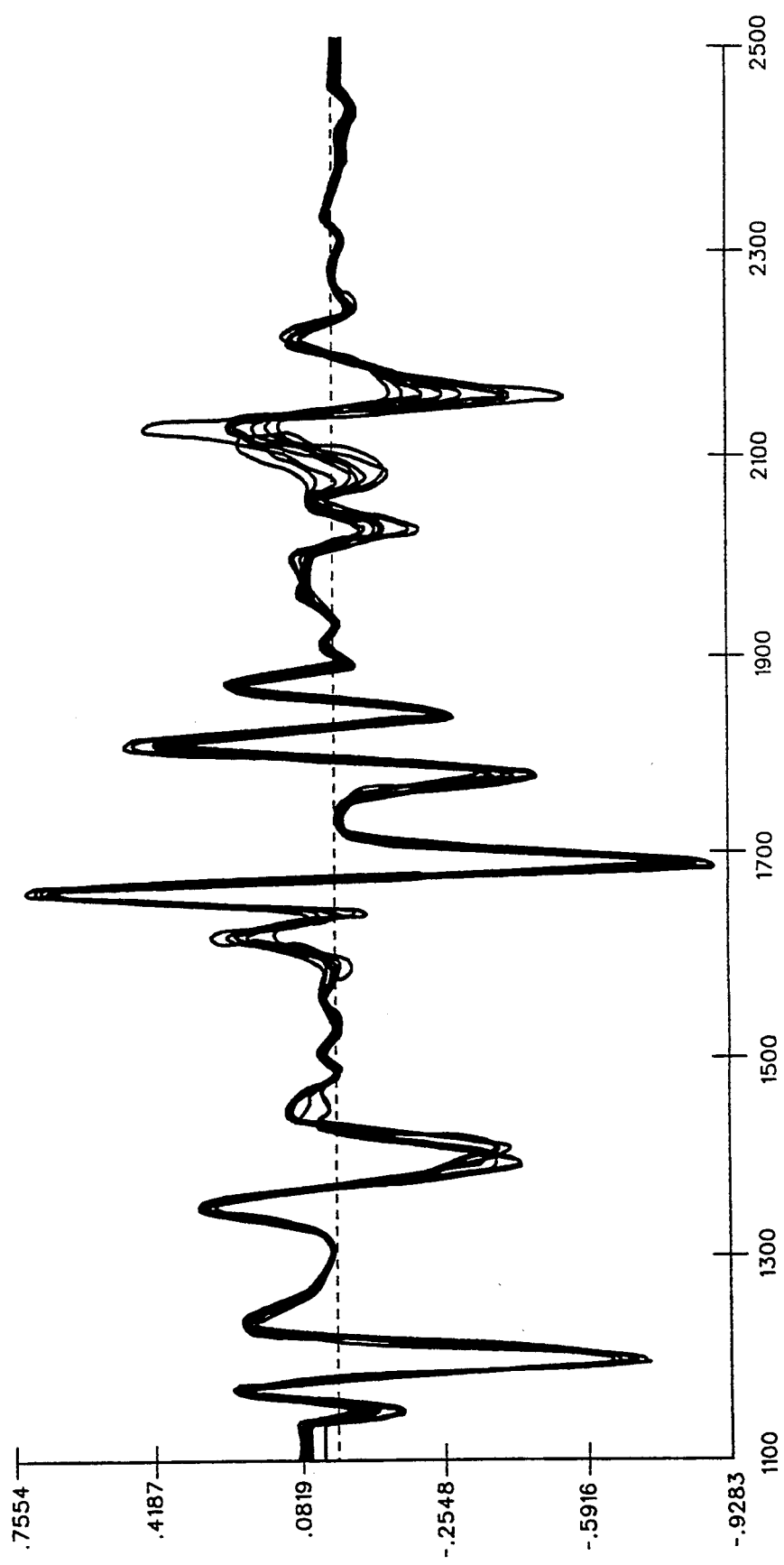

FIGS. 14 and 15 are plots of typical gasohol spectra for absorbance and second derivative of absorbance data (segment 20, gap 0). These figures show very little spectral variation in the region of 1308–1346 nm between the spectra where the ethanol content is substantially varied from 0–12 volume percent.

EXAMPLE 1

Example of One Method For Taking Finite Differences of Spectral Absorbances

Throughout this text we have referred to the use of derivatives of spectral absorbance data. Here we will show specifically what we mean when we use the term derivative. The logic used to take a derivative of spectral absorbance data is based on the calculus of finite differences since the data is expressed at regularly spaced intervals and is discontinuous in between the spaced intervals.

For spectral absorbance data we will use data gathered by a NIRSystems OL-6500. The OL-6500 has a spectral bandpass of about 9 nm but the spectral data is digitized such that recordings are displayed at 2 nm intervals. In general two things may be varied when the derivative about a point is calculated; the first of these is termed the segment and the second of these is termed the gap. The segment determines the number of points which are used to calculate the average number to the right and left of the point for which a derivative is being taken. The gap on the other hand refers to the number of points about the midpoint (immediately adjacent to the point where the derivative is being taken) which are excluded from the calculation of the adjacent segments (although the total segment length is unaltered). If we refer to the average value of the segment (higher wavelengths) above the point at which the derivative is being taken as A and the average value of the segment below the point where the derivative is taken as B, then according to the calculus of finite differences the first derivative of the point is A minus B.

For example, when the segment is 10 in 2 nanometer increments/segments and the gap is zero, the first derivative of the spectral absorbance ($d^1A/dw$) at 1170 nm is calculated as follows:

$$d^1A/dw_{1170} = \{(A_{1172} + A_{1174} + A_{1176} + A_{1178} + A_{1180})/5\} - \{(A_{1168} + A_{1166} + A_{1164} + A_{1162} + A_{1160})/5\}$$

If the segment is changed to six and the gap is changed to 8 the first derivative is:

$$d^1A/dw_{1170} = \{(A_{1176} + A_{1178} + A_{1180})/3\} - \{(A_{1164} + A_{1162} + A_{1160})/3\}$$

In a general way, for data occurring at two nanometer intervals the first derivative of spectral absorbance data at wavelength x is:

$$d^1A/dw_x = \Sigma(A_{w(x+(gap/2)+2i)})/(\text{segment}/2)$$
$$\Sigma - (A_{w(x-(gap/2)-2i)})/(\text{segment}/2)$$

In NIRSystems software package, NSAS (near infrared spectral analysis software, NIRSystems, Inc.,), for reasons which are unknown, the above equation is strictly only true for segments of 2, 6, 10, 14, 18 etc., and for gaps of 0, 4, 8, 12, 16, etc. A segment of 0 is treated as a segment of 2. Likewise a segment of 4 is treated as 6, etc. Similarly a gap of 2 is treated as a gap of 0, and a gap of 6 is treated as a gap of 4, etc.

Higher order derivatives may be simplified to expressions involving only first derivative terms and solved by the form of the previous equation. In general when the derivative being sought is of the h-th order:

$$d^hA/dw_x = d^{h-1}A/dw_{(x+\{(\text{segment}+gap)/2\}+1)} -$$
$$d^{h-1}A/dw_{(x-\{(\text{segment}+gap)/2\}-1)},$$

where the gap is equal to gap of the h-th ordered derivative and the segment used to calculate the (h-1)-th ordered derivative is the same as that being sought for the h-th ordered derivative.

For example, the 4th derivative of 1170 nm at a segment of 10 and a gap of 4 is:

$$\begin{aligned}
d^4A/dw_{1170} &= d^3A/dw_{1178} - d^3A/dw_{1162} \\
&= (d^2A/dw_{1186} - d^2A/dw_{1170}) - (d^2A/dw_{1170} - d^2A/dw_{1154}) \\
&= \{(d^1A/dw_{1194} - d^1A/dw_{1178}) - (d^1A/dw_{1178} - d^1A/dw_{1162})\} - \\
&\quad \{(d^1A/dw_{1178} - d^1A/dw_{1162}) - (d^1A/dw_{1162} - d^1A/dw_{1146})\} \\
&= \{\{[((A_{1198} + A_{1200} + \ldots + A_{1206})/5) - \\
&\quad (A_{1190} + A_{1188} + \ldots + A_{1182})/5)] \\
&\quad - [((A_{1182} + A_{1184} + \ldots + A_{1190})/5) - ((A_{1174} + A_{1172} + \ldots + A_{1166})/5)]\}
\end{aligned}$$

$$-\{[((A_{1182}+A_{1184}+\ldots+A_{1190})/5)-((A_{1174}+A_{1172}+\ldots+A_{1166})/5)]$$
$$-[((A_{1166}+A_{1168}+\ldots+A_{1174})/5)-((A_{1158}+A_{1156}+\ldots+A_{1150})/5)]\}$$
$$-\{[((A_{1182}+A_{1184}+\ldots+A_{1190})/5)-((A_{1174}+A_{1172}+\ldots+A_{1166})/5)]$$
$$-[((A_{1166}+A_{1168}+\ldots+A_{1174})/5)-((A_{1158}+A_{1156}+\ldots+A_{1150})/5)]$$
$$-\{[((A_{1166}+A_{1168}+\ldots+A_{1174})/5)-((A_{1158}+A_{1156}+\ldots+A_{1150})/5)]$$
$$-[((A_{1150}+A_{1152}+\ldots+A_{1158})/5)-((A_{1142}+A_{1140}+\ldots+A_{1134})/5)]\}\}$$

where all of the lower ordered derivatives are also taken using a segment of 10 and a gap of 4. Note that it is necessary to correct the segment and gap to a valid value before applying one of the generalized formulas (e.g. the fourth derivative at a segment of 8 and a gap of 6 is corrected to a segment of 10 and a gap of 4 before applying the formula).

Note segments of 2 nanometers were used, but segments of smaller or larger numbers or fractions of nanometers can be used. The choice preferably depends on the degree of spectral resolution available to the spectrometer.

EXAMPLE II

Temperature Dependence of Absorption Spectra and Their Corresponding Differentials In this example we will examine the relative temperature dependance of differing functional groups in the proximity of the first overtone of the hydroxyl group and second overtones of the aliphatic C—H groups (methyl, methylene, etc.). Table 1 shows some typical absorbance values for some of these functional groups in a single gasohol mixture, containing 9.47% ethanol by volume, measured at two different temperatures. Also shown is the absorbance at 1580 nm. This wavelength was reported to be useful for the determination of alcohols in gasoline by Wong and Jaselskis (Analyst, Volume 107, pp. 1282–1285, 1982). In Table I the absorbance spectra has been baseline corrected (set to equal 0 absorbance) at 1102 and 1314 nm to minimize changes due to baseline shifts. We have also included a values for the absorbance at 1384 nm for comparison.

Table 2 shows the value of the second derivative of absorbance (without baseline correction) for the same functional groups calculated from the same sample spectra used to construct Table 1 at the same two temperatures shown in Table 1. The derivative was calculated using a segment of 20 and a gap of 0. Some of the peak positions have been changed to coincide with the observed maxima in the derivative spectra. The 1580 nm reading has been changed to 1582 nm since this band is actually used in the present invention. However, because it is not a well defined peak in the absorbance spectra, it is hard to define the position as a distinct region in the second derivative spectra. Additionally we have included values for the second derivative of absorbance at 1314, and 1316 nm. We will discuss the significance of these peaks for the determination of oxygenates in a later example.

Table 3 shows a group of values which we are calling the temperature dependence for the differing functional groups. The values shown in Table 3 are calculated by subtracting the observed absorbance (or second derivative of absorbance) value at 33 degrees centigrade from the value at 19 degrees centigrade and dividing the result by the total change in temperature in degrees Fahrenheit (25.2 degrees Fahrenheit). For absorbance data the functional groups absorbance increases as the temperature decreases.

Table 4 shows the percent relative temperature dependence for the differing functional groups shown in Table 3. These numbers were generated by dividing the differences in absorbance (or second derivative of absorbance) at the lowest minus the highest temperature by the average absorbance (or second derivative of absorbance). The result was then divided by the temperature change in degrees fahrenheit and multiplied by 100. Mathematically this is the same as dividing the relative temperature changes shown in Table 3 by the average value shown in Tables 1 and 2 and multiplying by 100. Mathematically the calculation was performed as follows:

% relative temperature change =

$$\frac{100[(A_{23\ deg.\ C.}) - (A_{33\ deg.\ C.})]/(\text{avg.}\ A\ \text{at 23 and 33 deg. C.})}{(55.8\ \text{deg. F.})}$$

For the second derivative of absorbance data the A-terms in the above equation were merely replaced with the appropriate $d^2A/dw$-term.

The percent relative temperature change is an important property because it is an estimate of the percent error which could be expected in an absorbance (or second derivative of absorbance) reading for a change in temperature of 1 degree fahrenheit. Note that for the hydroxyl group (measured at 1580 nm) the percent relative temperature dependence is some 60 to 15 times higher than for aliphatic functional groups for absorbance and second derivative of absorbance data, respectively. For applications involving one wavelength equations (such as the Beer-Lambert Law) this error is also anticipated to be directly proportional to the error of the analytical determination (such volume % alcohol or weight % alcohol) if the regression constants at the wavelengths in question are the same.

While these errors might be small, the economic impact certainly is not. Consider a refinery making 100,000 barrels a day of gasohol (10% ethanol by volume). Suppose the refiner chooses to measure the amount of ethanol he is adding to his gasohol by NIR, and he decides to measure the ethanol using the baseline corrected absorbance at 1580 nm. If the temperature of the samples used to calibrate the NIR are 4 degrees fahrenheit higher than his average gasohol stream temperature, then Table 4 shows that he can expect to be 7.44% off on his ethanol determinations. This error, of course, is in addition to the other errors present during the calibration. If the cost of ethanol is 65 cents a gallon, after one year the refiner will have, solely from the temperature difference, lost 7.41 million dollars.

100,000 bbl/day×42 gal/bbl×365 day/year×0.1 gal ethanol/gal×0.65$/gal ethanol×0.0744
error=$7,410,000/year There are of course other errors which need to be considered such as the accuracy of the calibration, the degree of temperature control used on the gasohol stream, and the fraction of time the temperature controller is operational. The problem can also become more complex when one is trying to determine the weight percent oxygen in the gasoline when a variety of oxygenates are present.

It is a surprising and useful aspect of the present invention that the errors due to the temperature dependence of hydrocarbons and substituted hydrocarbons can be substantially minimized by the use of derivatives.

TABLE 1

The change in the observed value of the absorbance at three different temperatures for some important functional groups in the near infrared in gasoline/ethanol mixtures.

| Temperature deg. C. | Functional Group | Wavelength nm | Absorbance, AU |
|---|---|---|---|
| 19 | Methyl | 1192 | 0.90278 |
| 33 | Methyl | 1192 | 0.89445 |
| 19 | Methylene | 1210 | 0.59822 |
| 33 | Methylene | 1210 | 0.59143 |
| 19 | Aromatic | 1154 | 0.31042 |
| 33 | Aromatic | 1154 | 0.30799 |
| 19 | Hydroxyl | 1408 | 0.91480 |
| 33 | Hydroxyl | 1408 | 0.90945 |
| 19 | Hydroxyl | 1580 | 0.47654 |
| 33 | Hydroxyl | 1580 | 0.29560 |
| 19 | * | 1384 | 0.74359 |
| 33 | * | 1384 | 0.70008 |

*The shoulder of a methyl combination band (centered near 1360).

TABLE 2

The change in the observed value of the second derivative of absorbance at two different temperatures for some important functional groups in the near infrared in gasoline/ethanol mixtures.

| Temperature, deg. C. | Functional Group | Wavelength nm | Second of Derivative Absorbance, $d^2A/dw$ |
|---|---|---|---|
| 19 | Methyl | 1194 | −0.72469 |
| 33 | Methyl | 1194 | −0.71776 |
| 19 | Methylene | 1236 | 0.22525 |
| 33 | Methylene | 1236 | 0.22201 |
| 19 | Aromatic | 1146 | −0.02891 |
| 33 | Aromatic | 1146 | −0.02942 |
| 19 | Hydroxyl | 1404 | −0.39903 |
| 33 | Hydroxyl | 1404 | −0.45121 |
| 19 | Hydroxyl | 1580 | −0.02080 |
| 33 | Hydroxyl | 1580 | −0.01759 |
| 19 | * | 1314 | 0.03634 |
| 33 | * | 1314 | 0.03680 |
| 19 | * | 1316 | 0.04299 |
| 33 | * | 1316 | 0.04361 |
| 19 | * | 1384 | −0.28240 |
| 33 | * | 1384 | −0.24326 |

*The shoulder of a methyl combination band (centered near 1360).

TABLE 3

A comparison of the temperature dependance of different functional groups in the near infrared for gasoline/ethanol mixtures for absorbance and second derivative of absorbance data.

| Functional Group | Temperature Dependance for Absorbance Data, AU/deg. F.** | Temperature Dependance for Second Derivative of Absorbance Data, $(d^2A/dw)/$deg. F** |
|---|---|---|
| Methyl | 3.26E-04 | −2.75E-04 |
| Methylene | 2.69E-04 | 1.29E-04 |
| Aromatic | 9.64E-05 | 2.02E-05 |
| Hydroxyl | 2.12E-04 | 2.07E-03 |
| 1580 nm | 7.18E-03 | −1.27E-04 |
| 1314 nm | * | −1.82E-05 |
| 1316 nm | * | −2.46E-05 |
| 1384 nm | 1.73E-03 | −1.55E-03 |

*Too close to point used in baseline correction to be meaningful (baseline corrected at 1102 and 1314 nm).
**2.26E-04 and the like means 3.26 × 10⁻⁴ for all tables.

TABLE 4

A comparison of the relative temperature dependance of different functional groups in the near infrared for gasoline/ethanol mixtures for absorbance and second derivative of absorbance data.

| Functional Group | % Relative Temperature Dependance for Absorbance Data, (deg. F.)⁻¹ | % Relative Temperature Dependance for Second Derivative of Absorbance Data, (deg. F.)⁻¹ |
|---|---|---|
| Methyl | 3.63E-02 | 3.81E-02 |
| Methylene | 4.53E-02 | 2.87E-02 |
| Aromatic | 3.12E-02 | 6.94E-02 |
| Hydroxyl | 2.33E-02 | 4.87E-01 |
| 1580 nm | 1.86 | 6.64E-01 |
| 1314 nm | * | 4.99E-02 |
| 1316 nm | * | 5.68E-02 |
| 1384 nm | 2.39E-01 | 5.90E-01 |

*Too close to baseline correction to be meaningful (baseline corrected at 1102 and 1314 nm).

EXAMPLE III

This Example demonstrates the usefulness of the invention for gasohol mixtures. It compares the results of the present invention to the method of Wong and Jaselskis (Analyst, vol. 107, pp. 1282–1285, 1982) for the determination of the volume % ethanol in gasohol mixtures. Note that the magnitude of any observed temperature effect in a volume % ethanol regression model is a function of 3 factors. The first of these is the weighting constant of the temperature dependent term (the b-value), the second is the magnitude of the observed absorbance or mathematical transform thereof, e.g., first and higher finite difference derivatives, and the third is the % relative temperature dependency of the analytical wavelength. This can be seen from the equations shown below:

Volume % ethanol = constant + b(absorbance)
Magnitude of Temperature
Dependency = b(absorbance)(% relative temperature dependence)

For an h-th ordered derivative of absorbance $d^hA/dw$ merely replaces absorbance in the above equation. The "b" is a slope constant or linear coefficient of some absorbance value.

Table 5 shows the b-value, observed baseline offset corrected absorbance (at 1102 and 1314 nm), percent relative temperature dependency, and the predicted magnitude of observed temperature effects over the range of 1.568 to 1600 nm. This data was generated from observations on a set of 10 gasohol samples containing 0 to 11.37 percent ethanol by volume. The samples were prepared such that both the volatility grades and octane grades of the samples were substantially varied so that any matrix effects would be eliminated. This was done because if one used only one gasoline with differing amounts of ethanol added to it one might artificially induce correlations. For example a decrease in the amount of aromatic compounds might correlate to ethanol concentration even though there obviously should not be a direct relationship between the two components. The samples were prepared in accordance with ASTM Standard Practice D 4307 (ASTM Volume 5.O3, Petroleum Products and Lubricants, 1992 Annual Book of ASTM Standards, ASTM 1916 Race Street, Philadelphia, Pa.) using denatured 95.2% ethanol whose purity was confirmed by GC analysis.

Spectra of the 10 mixtures were then recorded on an NIRSystems OL-6500 near infrared spectrometer operating in reflectance mode using fiber optics over the wavelength range of 1100-2500 nm. The total path length was approximately 16 mm and the temperature of the samples was 19 degrees centigrade. The b-values shown in Table 5 were determined by preforming regression analysis on the data at 19 degrees centigrade. The same set of samples were rerun at a temperature of 33 degrees centigrade. The percent relative temperature dependency of the samples was then calculated, as described in Example II, using a 9.47% ethanol gasohol sample and the observed baseline offset corrected absorbances at the two temperatures. The magnitude of the observed temperature effect was then calculated by multiplying the b-value times the absorbance of the 9.47%, ethanol gasohol sample times the % relative temperature dependence.

Table 6 shows the results of the analysis when the second derivative of absorbance (without baseline correction) is substituted for the baseline offset corrected absorbance on the exact same spectra used to construct Table 5. The second derivative of the absorbance spectra was calculated using a segment of 20 and a gap of 0. The absorbance data occurred at 2 nm intervals. All of the calculations are identical to those used to construct Table 5 with the exception of substituting the second derivative of absorbance for the baseline offset corrected absorbance.

Table 7 shows the results that were obtained when regressions were preformed on the data at 19 degrees centigrade. The results of these regressions were also used to predict the percent ethanol in the same samples when they were rerun at 33 degrees centigrade. The bias shown in Table 7 is the average deviation of the samples from their known concentrations of ethanol.

The results shown in Tables 5, 6, and 7 shows that over this temperature range the magnitude of observed temperature effects is much larger for baseline offset corrected absorbance data than for the second derivative of absorbance data. This result could not have been anticipated.

The data in Table 4 shows at 1580 nm, assuming a one wave-length mode, only a 2.8 fold decrease in temperature variation, i.e., 1.86 versus 0.664. However, Tables 5, 6, and 7 which measure the magnitude of predicted and observed temperature effect on the calculated dependent variable, here percent ethanol, the effect found was generally at least 10 times smaller error. For example, at 1580 nm in Table 7, absorbance SEE went from 0.530 to 5.87, a ten fold increase in error. However, the derivative SEE at 1580 went from 0.371 to 0.443, a very small temperature caused error by comparison.

Likewise, it is surprising that regression analysis on the second derivative of absorbance data, even when measured under isothermal conditions, yields a lower standard error of estimate—and presumably lower standard of prediction—than does analysis of baseline offset corrected absorbance data. These two factors—lower errors and decreased temperature dependence—in addition to being surprising are valuable.

TABLE 5

A comparison of the predicted magnitude of temperature effects for baseline offset corrected absorbance data from 1568 to 1600 nm.

| Wavelength | b-value | 19 deg. C. absorbance | % relative temperature dependency | magnitude of predicted temperature effect (dependent variable 0/8 ethanol) |
|---|---|---|---|---|
| 1568 nm | 29.81 | 0.45289 | 1.85 | 2.50E-01 |
| 1572 nm | 29.37 | 0.46181 | 1.84 | 2.50E-01 |
| 1576 nm | 29.06 | 0.46987 | 1.85 | 2.53E-01 |
| 1580 nm | 28.90 | 0.47654 | 1.86 | 2.56E-01 |
| 1584 nm | 28.96 | 0.48195 | 1.88 | 2.62E-01 |
| 1588 nm | 29.27 | 0.48606 | 1.89 | 2.69E-01 |
| 1592 nm | 29.80 | 0.48890 | 1.91 | 2.78E-01 |
| 1596 nm | 30.59 | 0.49063 | 1.92 | 2.88E-01 |
| 1600 nm | 31.66 | 0.49192 | 1.97 | 3.07E-01 |

TABLE 6

A comparison of the predicted magnitude of temperature effects for second derivative of absorbance data from 1568 to 1600 nm.

| Wavelength | b-value | 19 deg. C. second derivative of absorbance | % relative temperature dependency | magnitude of predicted temperature effect |
|---|---|---|---|---|
| 1568 nm | −318.58 | 0.00628 | −0.0315 | 6.30E-04 |
| 1572 nm | −227.41 | −0.00610 | 0.602 | 8.35E-03 |
| 1576 nm | −178.57 | −0.01589 | 0.522 | −1.48E-02 |
| 1580 nm | −150.99 | −0.02080 | 0.664 | 2.08E-02 |
| 1584 nm | −135.12 | −0.01846 | 1.11 | 2.77E-02 |
| 1588 nm | −125.99 | −0.00587 | 7.70 | 5.69E-02 |
| 1592 nm | −120.19 | −0.02040 | −1.12 | −2.75E-02 |
| 1596 nm | −114.04 | 0.06184 | −0.437 | 3.08E-02 |
| 1600 nm | −103.28 | 0.11405 | −0.233 | 2.70E-02 |

TABLE 7

A comparison of baseline offset corrected absorbance to second derivative of absorbance results when the calibration equation is developed at 19 degrees centigrade and the same samples are reran as unknowns at 33 degrees centigrade.

| Wavelength Modeled | Type of Model | Standard Error of Estimate, 19 deg. C. | Correlation, 19 deg. C. | Standard Error of Prediction 33 deg. C. | bias |
|---|---|---|---|---|---|
| 1568 nm | Absorbance | 0.540 | 0.9914 | 5.75 | −0.65 |
| 1568 nm | Derivative | 0.873 | −0.9774 | 0.902 | −0.14 |
| 1572 nm | Absorbance | 0.540 | 0.9914 | 5.77 | −0.66 |
| 1572 nm | Derivative | 0.617 | −0.9888 | 0.647 | −0.20 |
| 1576 nm | Absorbance | 0.534 | 0.9916 | 5.80 | −0.67 |
| 1576 nm | Derivative | 0.461 | −0.9938 | 0.504 | −0.28 |
| 1580 nm | Absorbance | 0.530 | 0.9917 | 5.87 | −0.69 |
| 1580 nm | Derivative | 0.371 | −0.9959 | 0.443 | −0.36 |
| 1584 nm | Absorbance | 0.530 | 0.9917 | 5.98 | −0.71 |
| 1584 nm | Derivative | 0.335 | −0.9967 | 0.438 | −0.42 |
| 1588 nm | Absorbance | 0.535 | 0.9916 | 6.14 | −0.73 |
| 1588 nm | Derivative | 0.329 | −0.9968 | 0.461 | −0.49 |
| 1592 nm | Absorbance | 0.543 | 0.9913 | 6.35 | −0.76 |
| 1592 nm | Derivative | 0.329 | −0.9968 | 0.484 | −0.53 |
| 1596 nm | Absorbance | 0.557 | 0.9909 | 6.62 | −0.78 |
| 1596 nm | Derivative | 0.329 | −0.9968 | 0.658 | −0.53 |
| 1600 nm | Absorbance | 0.574 | 0.9900 | 6.96 | −0.81 |
| 1600 nm | Derivative | 1.07 | −0.9657 | 1.14 | −0.46 |

From Table 7, derivatives, especially second order finite difference derivatives such as discussed in Example 1 in the frequency range of 1576 to 1596 show an almost ten fold increase in Standard Error of Prediction in going from spectra taken at 19° C. to ones taken at 33° C. for raw absorbance in contrast to those for derivatives taken at the same temperatures.

EXAMPLE IV

This Example shows how to make use of the decreased temperature dependence of the hydroxyl band near 1580 nm to predict (R+M)/2 octane. This obviously is a concern for gasohol mixtures where temperature dependency of absorption bands is often very high.

A variety of methodologies have evolved to select wavelengths suitable for the calibration of a near infrared instrument. Techniques currently available include partial least square (PLS), multiple linear regression (MLR), principal component regression (PCR), and various techniques derived from these like PLS using autoscaling, PLS using mean centered data, and forward stepwise multiple linear regression. With the advent of high speed computers calibrations can be done almost automatically with a limited amount of user intervention. The pros and cons of some of these calibration methods have been summarized in a pair of articles by Haaland and Thomas (Anal. Chem., Volume 60, pp. 1193-1202 and pp. 1202-1208, 1988). As a result of this great significance is often placed on deriving a calibration where the highest possible correlation and lowest possible standard error of prediction are obtained.

As shown in the previous example with the gasohol mixtures, temperature dependency can greatly increase the total error of a calibration model. The effect of temperature on the calibration model increases under some circumstances the error of the model by more than an order of magnitude when the temperature varied by only 25.2 degrees fahrenheit. In situations where these errors are intolerable, such as gasoline blending where typically millions of dollars of product are involved daily, a successful approach will only be achieved when temperature dependency is examined as one of the fundamental parameters which controls the success of the calibration model.

To demonstrate the usefulness of the decreased temperature dependency of the 1580 nm region for the prediction of (R+M)/2 octane a calibration set of 72 gasohol samples were prepared. These samples covered the volatility range of 7 to 16 Reid vapor pressure units and an octane range of 86 to 93 (R+M)/2 octane. The samples were analyzed for (R+M)/2 octane by averaging the knock engine octane results of ASTM test methods I) 2699 and D 2700 (ASTM volume 5.04, Test Methods for Rating Motor, Diesel, and Aviation Fuels, 1989 Annual Book of ASTM Standards, ASTM 1916 Race Street, Philadelphia, Pa.) using the bracketing procedure. The ethanol content of the samples was substantially varied between 8-12 volume percent ethanol. The ethanol content of the gasohol samples is almost always specified at 10% by volume, however, we chose to vary the ethanol content in the calibration set because ethanol has a very high (R+M)/2 octane (over 110) and subtle variations in ethanol content can have a profound impact on a products octane.

After the samples had been prepared and analyzed by knock engine analysis their spectra were recorded over the wavelength range of 1100-2500 nm on a NIRSystems OL-6500 near infrared spectrophotmeter. The samples were run in reflectance mode using a total path length of approximately 16 mm. From the recorded spectra and octane analysis it was possible to develop a variety of calibration equations to model the dependent variable (R+M)/2 octane. Four PLS models were generated from the data using NSAS over the spectral range 1100-2200 (the last 300 nm of the recorded spectra were eliminated due to self absorption of the light by the low OH quartz fibers). The spectral data analyzed by the PLS algorithm included baseline offset corrected absorbance data (offset at 1102 and 1314 nm) with and without autoscaling, anti second derivative of absorbance data using a segment of 20 and a gap of zero with and without autoscaling. The optimum number of latent variables in the models were determined by a computer algorithm and the models were validated using a leverage correction. In addition, the baseline offset absorbance data was modeled using forward stepwise multiple linear regression at 1212, 1400, and 1216 nm, and by modeling the second derivative of absorbance data by regression analysis at 1224, 1582, and 1266 nm. The 1224 nm band in the second derivative regression model is the methyne band as shown in U.S. Pat. No. 4,963,745.

The methyne bands importance to gasohol samples octane was previously unknown prior to this work and was a surprise considering the octane contribution of the ethanol which does not contain any methyne groups. The methyne bands usefulness for the prediction of the octane of MTBE blends and hydrocarbon blends, however, is well established. As a result of this, and because of the redundant nature of the near infrared overtones—it is anticipated that the first and third overtones of the methyne band will also be found useful when combined with the different overtones of the hydroxyl group.

The correlations anti standard errors of estimate for the six different data treatments are summarized in Table 8. Notice that all of the models developed give lower standard errors of the estimate than were expected on the basis of the reproducibility of the primary knock engine test method and therefore all of the calibration equations generated are potentially useful.

The temperature dependencies of the octane models are harder to evaluate because temperature dependency has influenced all of the wave lengths. For the PLS models this would require 550 separate calculations. The variance of the temperature dependencies is likely to be additive and therefore should be calculable from the following equation:

$$\text{Magnitude of Temperature Dependency} = \Sigma\{[b_i(Absorbance_i)(\% \text{ Relative Temperature Dependency}_i)]^2\}^{0.5}$$

where the contributions for b, absorbance (or second derivative of absorbance), and % relative temperature dependency are for the i-terms used to develop the calibration equation.

To show how the evaluation can be made consider the 3 wavelength regression model using the second derivative of absorbance data at 1224, 1582, and 1266 nm, respectively. For this data $b_1$, $b_2$ and $b_3$ equal 141.097, −80,345 and −154.131, the second derivatives of absorbance are 0.15591, −0.02070, and 0.06843 at 19 degrees centigrade, and the % relative temperature dependencies are 0.0235, 0.811, and 0.00580, respectively at 1224, 1582, and 1266 nm. According to above equation the magnitude of the temperature dependency is expected to be 0.0145 with the majority of the temperature variance resulting from the contribution of the 1582 nm term. By comparison to the results shown in Example III for the one wavelength temperature dependencies we conclude that this equation should be useful for predicting (R+M)/2 octane both in terms of calibration errors and errors arising from temperature effects.

To further evaluate the temperature dependency of the calibration models we have analyzed a set of gasohol samples measured at two different temperatures. The spectra were recorded as before at 19 and 33 degrees centigrade. A comparison was then made between the differences in predicted octanes at the two temperatures. These results are summarized in Table 9.

It can be seen in Table 9 that all of the models with the exception of regression model on second derivative of absorbance data and the 6 factor PLS model using second derivative data and autoscaling show severe temperature effects. It is further presumed that the 6 factor PLS models relative temperature independence is more a result of chance than it is the result of a carefully thought out data manipulation. Still it does point out that there does exist some number of calibration equations which are relatively temperature independent simply by chance. But the results of this example clearly show that when the results are critical it is far better to control the potential difficulties beforehand, with a judicious choice of wavelength selections, than to leave the results to chance.

TABLE 8

A comparison of the results generated six different by the six different calibration methods for (R + M)/2 octane of gasohol.

| Type of Data | Type of Model | Correlation with (R + M)/2 Octane | Standard Error of Estimate |
| --- | --- | --- | --- |
| Baseline offset corrected absorbance | 5 Latent Variable PLS with no scaling | 0.9944 | 0.212 |
| Baseline offset corrected absorbance | 6 Latent Variable PLS with Autoscaling | 0.9960 | 0.180 |
| Second Derivative | 5 Latent Variable PLS with no scaling | 0.9946 | 0.207 |
| Second Derivative | 6 Latent Variable PLS with Autoscaling | 0.9960 | 0.180 |
| Baseline offset | 3 wavelength MLR stepwise regression | 0.9900 | 0.277 |
| Second Derivative | 3 wavelength MLR using 1580 nm | 0.9953 | 0.190 |

TABLE 9

A comparison of the differences in the predicted (R + M)/2 octane when the same gasohol samples are run and predicted at 19 and 33 degrees centigrade.

| Type of Data | Type of Model | Standard Error of Difference | Bias |
| --- | --- | --- | --- |
| Baseline offset corrected absorbance | 5 Latent Variable PLS with no scaling | 10.5 | −0.097 |
| Baseline offset corrected absorbance | 6 Latent Variable PLS with Autoscaling | 8.59 | 0.403 |
| Second Derivative | 5 Latent Variable PLS with no scaling | 0.056 | 0.147 |
| Second Derivative | 6 Latent Variable PLS with Autoscaling | 0.350 | 0.816 |
| Baseline offset | 3 wavelength MLR stepwise regression | 8.91 | 0.562 |
| Second Derivative | 3 wavelength MLR using 1580 nm | 0.156 | −0.227 |

The value of second derivative alone and in conjunction with the 1580 nm band is clear.

EXAMPLE V

This Example demonstrates another wavelength region which was found to be highly useful for determining total percent oxygen in gasoline. Oxygenate content, expressed as weight percent O, will soon become a specification for motor fuels sold in ozone and carbon monoxide non-attainment areas within the United States.

That NIR is not likely to be useful for an indirect method for determining total oxygenate content, is clear from a fact which Weyer has pointed out in Applied Spectroscopy Reviews, 21(1&2), pp. 2, 1985. Weyer notes that the first overtone of the C—O stretch occurs in the mid infrared and not in the near infrared. Thus, since the intensity of overtones diminishes sharply with each overtone these higher overtones occur near other bands involving primary C—H overtones, the C—O overtones observable in the near infrared would be expected to faint at best. Further, since quartz fibers absorb light in this region, such interference makes these bands even less likely to be observed.

Still, because of the advanced calibration algorithms, such as PLS, which can presumably model even minor spectral changes that occur, there might be enough variance to model oxygenate content. Surprisingly, there was found a distinct spectral region between 1300–1346 nm where total oxygenate content was modeled and optimized using a second derivative with a segment of 20 and a gap of 0. The same band, but with lower observed correlation to total oxygenate content, can be observed in the baseline offset absorbance spectra and in the first, third, and higher order derivatives.

Table 10 shows some of the observed one wavelength correlations in the region of 1308 to 1346 nm using a variety of data pretreatments on a set of 56 oxygenated motor fuels containing from 0 to 4% total oxygen by weight. The oxygenates included with these samples include methanol, isopropanol, t-butyl alcohol, methyl t-butyl other (MTBE), ethyl t-butyl ether (ETBE), and t-amyl methyl ether (TAME). Ethanol was not included, but it has been studied separately with MTBE and the same general behaviors were observed. The samples were prepared in accordance with ASTM Standard Practice D 4307 and the spectra were recorded on an OL-6500 NIRSystems spectrophotometer at a path length of 16 nm. The samples were converted to weight percent oxygen by multiplying the amounts of the oxygenates added by their gravimetric conversion factors (atomic weight of oxygen divided the molecular weight of the oxygenate) and multiplying the result times the weight percent purity of the oxygenate times 100. The volatility range and octane range of pre-oxygenated gasoline samples were substantially varied to eliminate any matrix effects. Analysis of the samples by a variety of calibration algorithms, including partial least squares analysis, with and without autoscaling, forward stepwise multiple linear regression, and regression modeling were accomplished on both the baseline offset corrected absorbance spectra and second derivative of absorbance. The PLS models used a leverage correction validation method and were performed over 1100–2200 nm. Furthermore during the regression modeling attempts were made to optimize the second derivative of absorbance model using the 1314–1316 nm wavelengths. This resulted in a model being generated using 1316, 1196, and 1240 nm.

The results of the analysis showed that standard errors of estimate between 0.11 and 0.38 weight percent oxygen for all of the data treatments using 5 latent variable PLS models and 3 wavelength regression models. The best correlations were observed for the partial least squares analysis of second derivative without autoscaling, the partial least squares analysis of the baseline offset absorbance using autoscaling, and the optimized 3 wavelength regression model. These models showed standard errors of prediction of 0.11, 0.14 and 0.17 weight percent oxygen, respectively. Examination of the weightings used in the PLS models again showed very low weightings in the region of 1316 nm for the data without autoscaling and only modest weightings in the vicinity of 1316 for the autoscaled weightings. This is shown graphically in FIGS. 10, 11, 12, and 13.

To examine the effect of temperature on the different pretreatments and calibration techniques a set of 20 samples containing ethanol and MTBE were used to develop calibrations on the samples whose spectra were recorded at 20 degrees centigrade. The PLS models were developed using 5 latent variables per model and the optimized regression model was developed using 1316 and 1156 nm. Next the same samples were rerun at 34 degrees centigrade and analyzed as unknowns. The exact temperatures of the samples varied by approximately 2 degrees centigrade during the analysis at each temperature. The same types of data treatments as described above were performed on the 20 degree data and the equations were used to make predictions on the 34 degree spectral data. The results are summarized in Table 11.

While none of the results shown in Table 11 show the level of improvement seen in the other models the temperature effect for the regression model developed and optimized using the 1316 nm wavelength were found at the minimum approximately as good, both in terms of calibration error and reduced temperature dependency, as any of the other calibration models which were developed.

The results are exciting, surprising, unexpected and valuable. It could not have been anticipated that the 1308–1346 nm would correlate so well with oxygenate content because as Kelly and Callis have pointed out (Jeffrey J. Kelly and James B. Callis, Anal. Chem., vol. 62, pp. 1446) the closest band near this region is a methyl combination band near 1360 nm, and therefore this region should have significant overlap from other types of molecules in the gasoline mixtures, such as paraffins and isoparaffins, which should prohibit this region from being analytically useful. It is believed that this might be explainable, however, by an inductive effect between the oxygenates oxygen and nearby methyl groups. Still, because of the differing number of methyl groups in the oxygenated molecules the effect would have been expected to have been obscured if the compounds had similar molar absorptivities since the observed bands would have had differing absorbances, and therefore derivatives of absorbance, arising from the differences in the number of methyl groups per molecule.

This 1308–1346 nm region is also surprising from the fact ethers and alcohols oxygen content can be predicted using the same wavelengths, with a minimal amount of temperature dependence, even though the two types of molecules have differing amounts of percent relative temperature dependence. For example, a 2.43 weight % oxygen sample of a gasohol mixture was found to have a percent relative temperature dependency of −0.0551 at 1316 nm, but a 2.36 weight % oxygen MTBE in gasoline sample had a −0.236 percent percent relative temperature dependency.

Another advantage of the NIR oxygenate method as presented in this invention arises from the lack of specificity of the method for individual oxygenates. While this could be viewed as a drawback, this method offers the advantage that, within limits, all of the oxygenated components in the gasoline will be determined simultaneously. For example, the MTBE, used in the experiments contained 95.320% MTBE by weight which is very high in purity for industrial use. Still, this sample also contained 0.683 weight percent t-butanol, 1.004 percent sec-butylmethyl ether, and 0.120 weight percent TAME, whose oxygenate content would have been overlooked by a method specific for MTBE.

1308–1346 nm range is useful for the determination of octane especially where mixtures of oxygenates are involved, where the octane contribution of the oxygenate can not be deduced in other areas of the near infrared spectrum.

Throughout these examples we have shown how PLS models can be used to determine oxygenate content and octane utilizing wavelengths in the range of 1560–1600 nm and 1308–1346 nm and a variety of other benefits, such as decreased temperature dependency, which can be derived from their use. However, it should be pointed out that only with autoscaling, were any significant contributions in terms of weightings observed for the oxygenate determinations, and for octane determinations weightings in the range of 1560–1600 were moderate for both the autoscaled and non-scaled regressions. As a result of this it is envisioned that this invention will teach those of skill in the art who use global statistical techniques, such as PLS and PCR, to optimize these wavelength ranges when calibration equations are developed using these techniques so that they might also derive the benefits of this invention. For modeling on non-scaled data this can be accomplished by leaving out portions of the spectrum where temperature dependencies are high.

For autoscaled data Haaland and Thomas have written (Anal. Chem., Vol. 60(11), pp. 1197, first full paragraph) that "However, it must be stressed that the results of the PLS analysis depend on the nature of the scaling of the spectral data, and different results are to be expected depending on how the spectral data are pretreated (this is true of PCR also). Therefore, it may not be appropriate to scale spectral data if, as is often the case, the errors are independent of the magnitude of spectral intensity changes. Autoscaling can also degrade the results if much of the data contain spectral regions with little or no spectral variation. In this case, data with minimal spectral variation will contain primarily noise but will be given the same importance in the analysis as data which experiences composition-related variations. On the other hand, autoscaling may also be useful for deemphasizing the effects of chemical components with large spectral features that may not be of interest in the analysis." FIGS. 14 and 15 are plots of typical gasohol spectra for absorbance and second derivative of absorbance data (segment 20, gap 0). These figures show very little spectral variation in the region of 1308–1346 nm between the spectra where the ethanol content is substantially varied from 0–12 volume percent. Thus the teachings of Haaland and Thomas, would lead those skilled in the art not to autoscale the data used for PLS or PCR model, or perhaps even to remove the 1308–1346 nm range from the wavelengths used in the PLS or PCR model. In fact Haaland and Thomas arguments would lead one of skill in the art to believe that autoscaling of the spectra should not be done in either the 1308–1346 nm range or the 1560–1580 nm range because, in addition to the above, the errors which are observed are indeed independent of the magnitude of the observed spectral intensity changes. The errors of all of the calibration models are in fact substantially equal for all of the results presented, whether the oxygenate content is relatively high, or low. For example using the one wavelength models near 1580 nm to predict volume percent ethanol the error at 0 percent (low spectral intensity) were substantially equal to those samples containing 12 percent (high spectral intensity).

Thus the art teaches away from the invention. This invention demonstrates the usefulness of 1308–1346 and 1560–1600 with PLS and PCR.

The value of the method can be realized by comparing the NIR results to the existing ASTM GC test method D4815 (ASTM, Volume 5.03, ASTM 1916 Race Street, Philadelphia, Pa., 1992). The D4815 method shows that for six percent by volume solutions of alcohols and MTBE repeatabilities vary from 0.03 to 0.52 volume percent and reproducibilities vary from 0.68 to 2.50 percent at the 95% confidence limits, respectively. Thus, the errors by the GC method, at 95% confidence, are from greater than 10 percent to 40% relative to the total amount of alcohol or MTBE present based on the reproducibility statement of D4815. By the invention shown within these examples, however, we can anticipate errors, at the 95% confidence limit, of about 6% for volume % ethanol and about 10% for weight percent oxygen in terms of absolute accuracy (determined from the amount of oxygenate weighed into the gasoline). These results clearly demonstrate the value of NIR for determining the oxygenate content of gasoline mixtures. This could especially be true when the total 0.24 oxygenate content is desired (and the GC errors must be summed).

TABLE 10

Some one wavelength correlations with total oxygenate content. All derivatives show have a gap of 0.

| Pretreatment | Wavelength | Segment | Correlation | Standard Error of Estimate |
|---|---|---|---|---|
| Baseline offset absorbance | 1346 nm | — | 0.9561 | 0.474 |
| First Derivative | 1334 nm | 4 | 0.8529 | 0.589 |
| First Derivative | 1334 nm | 10 | 0.8767 | 0.542 |
| First Derivative | 1328 nm | 20 | 0.8996 | 0.492 |
| First Derivative | 1322 nm | 30 | 0.8645 | 0.567 |
| Sec. Derivative | 1324 nm | 10 | 0.8837 | 0.528 |
| Sec. Derivative | 1316 nm | 20 | 0.9670 | 0.287 |
| Sec. Derivative | 1308 nm | 30 | 0.8645 | 0.486 |
| Third Derivative | 1344 nm | 10 | −0.8192 | 0.647 |
| Third Derivative | 1338 nm | 20 | −0.8626 | 0.570 |
| Third Derivative | 1294 nm | 30 | 0.7846 | 0.699 |

TABLE 11

Results of predicting the oxygenate content of ethanol and MTBE gasoline mixtures when the calibration is developed at 20 degrees centigrade and the samples are reran at 34 degrees centigrade.

| Type of Model | Pretreatment | Standard Error of Estimate at 20 deg. C. | Standard Error of Prediction at 34 deg. C. | Bias |
|---|---|---|---|---|
| PLS with autoscaling | Second Derivative | 0.165 | 0.261 | 0.247 |
| PLS without autoscaling | Second Derivative | 0.099 | 0.307 | 0.170 |
| PLS with autoscaling | Offset Absorbance | 0.210 | 0.561 | 0.063 |
| PLS without autoscaling | Offset Absorbance | 0.112 | 0.576 | 0.106 |
| Forward Stepwise Regression | Offset Absorbance | 0.156 | 0.246 | 0.540 |
| Regression Optimization | Second Derivative | 0.129 | 0.222 | 0.300 |

MODIFICATIONS

Specific compositions, methods, or embodiments discussed are intended to be only illustrative of the invention disclosed by this specification. Variation of these compositions, methods, or embodiments are readily apparent to a person of skill in the art based upon the teachings of this specification anti are therefore intended to be included as part of the inventions disclosed herein.

Reference made anywhere in this specification to patents or literature is intended to result in such patents or literature being expressly incorporated herein by reference.

What is claimed is:

1. A method for controlling total oxygenate content of a composition that comprises at least 1% by volume of oxygenate content, comprising in combination the steps:
   a. measuring the value of at least one absorbance in at least one wavelength between about 1,300 to 1,350 nanometers; and
   b. substituting said value into an equation to obtain a prediction of oxygenate content of said composition, whereby the effect of temperature on said prediction is reduced; and
   c. controlling said composition in response to said prediction.

2. The improved method of claim 1, wherein said valve is measured at at least one other wavelength within the infrared spectrum of said composition, whereby the temperature dependence of said prediction of oxygenate content is reduced or the Standard Error of Estimate for said prediction of oxygenate content is improved.

3. The improved method for claim 2, wherein said at least one other absorbance band which reduces temperature dependence comprises using frequencies that involve C-H stretching or bending vibrations.

4. The improved method of claim 1 wherein oxygenate content involves oxygen present in species selected from the group consisting of: alcohols and ethers.

5. The improved method of claim 4 wherein the alcohols and ethers are selected from the group consisting of methanol, ethanol, propanol, iso-propanol, n-butanol, isobutanol, t-butanol, iso-amyl alcohol, t-amyl alcohol, methyl t-butyl ether, ethyl t-butyl ether, methyl iso-amyl ether, ethyl iso-amyl ether, methy t-amyl ether, and ethyl t-amyl ether.

6. The improved method of claim 1, wherein said value is changed by a mathematical transformation prior to substitution into said calibration equation.

7. The improved method of claim 6, wherein said mathematical transformation of said at least one absorption band in the near infrared involves a finite difference derivative having a number of segments in the range 6 to 25 and a gap in the range 0 to 5.

8. The improved method of claim 7 wherein said number of segments is in the range 15 to 25.

9. An improved method for controlling octane of a composition that contains at least 1% by volume of an alcohol, comprising in combination:
   a. measuring the absorbance of said composition in at least one band in the infrared spectrum;
   b. transforming said absorbance by a mathematical transformation comprising taking its derivative of first or higher order
   c. substituting said derivative into an equation which provides a prediction to predict octane of said composition and
   d. controlling blending of components, including said alcohol, which affect the octane of said composition, in response to said prediction.

10. The improved method of claim 9 wherein said at least one absorption band is selected from the group consisting of a first band in the range 1576 to 1596 nm.

11. The improved method of claim 10, wherein there is an additional absorption band in the range 1140 to 1266 nm that is also used in said calibration equation.

12. The improved method of claim 10, wherein said absorbance is measured at at least one other wavelength in the range 1576 to 1596 nm and is transformed into a finite difference derivative of at least first order prior to use in said calibration equation.

13. The improved method for claim 9 wherein said frequencies that involve C—H stretching or bending vibrations, comprise methyne bands and their overtones.

14. An improved method for controlling alcohol content of an at least 1% by volume oxygenate-containing composition comprising:
   a. measuring absorbance in an infrared band in the range 1576 to 1596 nm;
   b. transforming said absorbance by a mathematical transformation;
   c. substituting said absorbance so changed into an equation which defines a prediction of values representative of alcohol content of said composition; and
   d. controlling blending of said composition in response to said prediction.

15. The improved method of claim 14, wherein said mathematical transformation is at least a first order finite difference derivative.

16. The improved method of claim 15, wherein said at least first order finite difference derivative involves a number of segments in the range 4 to 30 and a gap in the range 0 to 4.

17. The improved method claim 16 wherein number of segments is in the range 15 to 25.

18. The improved method of claim 14, wherein at least one other infrared spectral absorbance of said oxygenate-containing composition is selected from frequencies which reduce temperature dependence or which improves the Standard Error of Estimate for said alcohol content.

19. An improved method for controlling alcohol content of an at least 1% by volume oxygenate-containing composition comprising:
   a. measuring absorbance in an infrared band in the range 1310 to 1340 nm;
   b. transforming said absorbance by a mathematical transformation;
   c. substituting said absorbance so changed into an equation which defines a prediction of values representative of alcohol content of said composition; and
   d. controlling blending of said composition in response to said prediction.

20. The improved method for determining octane of claim 19, wherein said at least one absorption band is changed by a mathematical transformation prior to use in a calibration equation from which values representative of said octane are defined in relation to said at least one mathematically transformed absorption band.

21. The improved method for determining octane of claim 20, wherein said mathematical transformation is selected from a group consisting of finite difference derivatives of first and higher orders.

22. The improved method for determining octane of claim 19, wherein there is additionally used an absorbance within the spectrum of absorbances for said composition corresponding to a band selected from a methyne band and their overtones determined by taking at least first order finite difference derivatives of said spectrum.

* * * * *